US005935897A

United States Patent [19]

Trübenbach et al.

[11] Patent Number: 5,935,897

[45] Date of Patent: *Aug. 10, 1999

[54] MONOMODAL AND POLYMODAL CATALYST SUPPORTS AND CATALYSTS HAVING NARROW PORE SIZE DISTRIBUTIONS AND THEIR PRODUCTION

[75] Inventors: Peter Trübenbach; Alfred Hagemeyer, both of Ludwigshafen; Günter Lauth, Ratzenburg; Uwe Dingerdissen, Seeheim-Jugenheim; Franz Josef Bröcker, Ludwigshafen; Klemens Flick, Herxheim, all of Germany

[73] Assignee: BASF Aktiengesellschaft, Ludwigshafen, Germany

[ * ] Notice: This patent is subject to a terminal disclaimer.

[21] Appl. No.: 08/711,043

[22] Filed: Sep. 10, 1996

[30] Foreign Application Priority Data

Sep. 12, 1995 [DE] Germany .......................... 195 33 484

[51] Int. Cl.[6] ..................................................... B01J 23/00

[52] U.S. Cl. .................... 502/527.14; 502/300; 502/150; 502/174; 502/173; 502/232; 502/63; 502/177; 502/200; 502/159; 502/162; 502/167; 502/168; 502/201; 502/208; 502/217; 502/344; 502/352; 502/325; 502/326; 502/339; 502/345; 502/349; 502/355; 502/303; 502/319; 502/350

[58] Field of Search .................................... 502/300, 150, 502/174, 173, 232, 63, 177, 200, 159, 162, 167, 168, 201, 208, 217, 344, 352, 325, 326, 339, 345, 349, 355, 303, 319, 350, 527.14

[56] References Cited

U.S. PATENT DOCUMENTS

| | | | |
|---|---|---|---|
| 3,755,204 | 8/1973 | Sergeya | 252/455 R |
| 4,032,433 | 6/1977 | Petri et al. | 208/112 |
| 4,356,113 | 10/1982 | Lim et al. | 252/455 Z |
| 4,536,358 | 8/1985 | Welsh et al. | 264/81 |
| 5,145,900 | 9/1992 | Sterzel et al. | 524/404 |
| 5,191,144 | 3/1993 | Le et al. | 585/643 |
| 5,198,489 | 3/1993 | Sterzel et al. | 524/439 |
| 5,217,930 | 6/1993 | Dubots | 501/88 |
| 5,304,364 | 4/1994 | Costa et al. | 423/338 |
| 5,322,821 | 6/1994 | Brezny | 501/80 |
| 5,342,561 | 8/1994 | Sterzel et al. | 264/49 |
| 5,384,290 | 1/1995 | Brenzy | 501/81 |
| 5,395,808 | 3/1995 | Miller et al. | 502/7 |
| 5,460,759 | 10/1995 | Dubots | 264/29.7 |

FOREIGN PATENT DOCUMENTS

| | | |
|---|---|---|
| 0413231 | 2/1991 | European Pat. Off. . |
| 0513500 | 11/1992 | European Pat. Off. . |
| 0603990 | 8/1994 | European Pat. Off. . |
| A-292149 | 7/1991 | Germany . |
| 4120687 | 1/1993 | Germany . |
| 1458961 | 12/1976 | United Kingdom . |

OTHER PUBLICATIONS

Despeyroux et al, “Auf den Trager kommt es an ”, Chem. Ind. vol. 10, 1993, no month, pp. 48–49 (no translation).

Hammon et al, “Fabrication of pellets with defined pore–size distribution”, Chem. Ing. Tech., vol. 56 (1984), no month, pp. 455–466 (English abstract only, see p. 455).

*Primary Examiner*—Virginia Manoharan
*Assistant Examiner*—Nadine Preisch
*Attorney, Agent, or Firm*—John H. Shurtleff

[57] ABSTRACT

Monomodal or polymodal catalyst supports or catalysts having a BET specific surface area of from 0.01 to 250 $m^2/g$ and a monomodal or polymodal pore size distribution having a mean pore diameter of from 50 to 300,000 nm measured by the mercury pressure porosimetry method, wherein a) from 10 to 95% of the pore volume is at from 0.2 to 100 times the mean pore diameter and/or b) from 10 to 80% of the pore volume is at from 0.8 to 100 times the mean pore diameter and/or c) from 50 to 95% of the pore volume is at from 0.2 to 1 times the mean pore diameter and/or d) from 50 to 80% of the pore volume is at from 0.8 to 1 times the mean pore diameter and e) the width at half height of the pore size distribution is less than 0.6 times the mean pore diameter, which are useful for the preparation of chlorine from hydrogen chloride in a non-steady-state Deacon process, for the reaction of ethylbenzene to give styrene in a non-steady-state oxydehydrogenation, for preparing aziridine from ethanolamine, in reductions, hydrogenations, oxidations, dehydrogenations, acid- or base-catalyzed reactions or reactions in a fluidized bed, for removing combustion residues from diesel exhaust gases and for removing $NO_x$ from waste gases, in bioreactors together with bacteria and as biocatalyst supports with immobilized enzymes or microbes, and a process for producing said monomodal or polymodal catalyst support or catalyst.

9 Claims, 9 Drawing Sheets

MONOMODAL AND POLYMODAL CATALYST SUPPORTS AND CATALYSTS HAVING NARROW PORE SIZE DISTRIBUTIONS AND THEIR PRODUCTION

The present invention relates to catalyst supports and catalysts having a narrow pore size distribution, a process for their production and their uses.

U.S. Pat. No. 5,191,144 discloses zeolites having a very uniform pore size from 0.2 to 1 nm which can be varied in the micropore range (<2 nm), produced by hydrothermal synthesis. Owing to the low pore size, the size of molecules which can be reacted is restricted. Since an $SiO_2$ binder is used in zeolites, these zeolites are stable only to 700° C. and not chemical-resistant above 400° C., and their mechanical stability is poor. In addition, the zeolites have very acid surfaces, which limits their use to acid-catalyzed reactions.

Chem. Ind., 10 (1993) 48–49 discloses a process for producing catalyst supports in the mesopore range (from 2 to 50 nm) from pyrogenic oxides ($SiO_2$, $Al_2O_3$, $TiO_2$, $ZrO_2$) by reacting the halides in an oxyhydrogen flame. The pore sizes of the supports are from 10 to 70 nm, with no pores being formed in the range less than 8 nm. However, the pore distributions are broad.

Chem. Ing. Tech., 56 (1984) 455–463 discloses melamine as macropore former. However, pyrolysis leads to crack formation.

U.S. Pat. No. 3,755,204 discloses porous ceramic bodies produced by shaping a mixture of ceramic powder, a polyolefin (polyethylene copolymer) and a plasticizer (mineral oil, diethylene glycol, polyvinyl alcohol, polyvinylpyrrolidone), pyrolysis and sintering. The cracks occurring in the ceramic body during pyrolysis can be avoided by extraction of the plasticizer with aqueous surfactant solutions (DE-A-24 59 475). These are ceramic honeycomb bodies in which the open pores are introduced as channel structures by the thermoplastic shaping.

DE-A-24 59 475 discloses a process for producing shaped porous metal structures in which a mixture of metal powder, polyolefin and a plasticizer is compounded and the plasticizer is leached from the mixture using a solvent prior to pyrolysis.

DE-A-41 20 687 discloses porous sintered parts of metal or ceramic, produced using a polyolefin, a plasticizer and an additive which is not miscible with the binder system. The additive is a vinylaromatic copolymer based on polystyrene which is introduced at a particle size of from 20 to 250 μm as a spacer between the metal or ceramic particles. Variation of the additive particle size enables different but unspecified pore sizes to be produced. The pore size distribution is bimodal and broad, since the pores are formed, on the one hand, by the particle size distribution of the additive and on the other hand by the interstitial spaces between the metal or ceramic particles.

EP-A-446 708 discloses the production of dense metallic shaped parts and EP-A-444 475 discloses the production of dense ceramic shaped bodies via the shaping of thermoplastic compositions.

EP-A-413 231 discloses a process for producing dense inorganic sintered shaped parts, in which green bodies of sinterable powders and polyoxymethylene or a copolymer containing a predominant proportion of oxymethylene units as binder are shaped by extrusion or injection molding. The binder is removed quickly, without cracking and without distortion from these green parts by treatment with a gaseous acid or boron trifluoride. The binder-free porous parts have a very low mechanical stability and are sintered to full density. This route is used to produce dense, ceramic or metallic structural materials or functional materials having a complicated shape, which are not suitable as catalyst supports or catalysts.

Sinterable organic polymers such as Teflon (EP-A-513 500), polyimide or unplasticizable polymers (EP-A-517 025) can also be processed into dense components using this production method.

It is known from DE-A-41 20 687 that it is very difficult to reproducibly produce mechanically stable parts having a constant pore distribution from very fine metal or ceramic powders (particle size about 1 μm) using the known processes.

It is an object of the invention to provide a solution to the abovementioned drawbacks.

We have found that this object is achieved by novel and improved monomodal or polymodal catalyst supports or catalysts having a BET specific surface area of from 0.01 to 250 $m^2/g$ and a monomodal or polymodal pore size distribution having a mean pore diameter of from 50 to 300,000 nm measured by the mercury pressure porosimetry method, wherein a) from 10 to 95% of the pore volume is at from 0.2 to 100 times the mean pore diameter and/or
b) from 10 to 80% of the pore volume is at from 0.8 to 100 times the mean pore diameter and/or
c) from 50 to 95% of the pore volume is at from 0.2 to 1 times the mean pore diameter and/or
d) from 50 to 80% of the pore volume is at from 0.8 to 1 times the mean pore diameter and
e) the width at half height of the pore size distribution is less than 0.6 times the mean pore diameter, and also a process for their production by shaping a mixture of A) from 15 to 70% by volume of
   I) an inorganic powder selected from the group of oxides, nitrides, carbides, silicates, aluminosilicates of the elements beryllium, magnesium, calcium, strontium, barium, boron, aluminum, gallium, indium, thallium, silicon, germanium, tin, lead, antimony, selenium, tellurium, polonium, astatine, iron, cobalt, nickel, ruthenium, rhodium, palladium, osmium, iridium, platinum, copper, silver, gold, zinc, cadmium, mercury, scandium, yttrium, lanthanum, actinium, titanium, zirconium, hafnium, vanadium, niobium, tantalum, chromium, molybdenum, tungsten, manganese, technetium, rhenium, cerium, praseodymium or mixtures thereof and/or
   II) a metallic powder selected from among metals and alloys of the elements boron, aluminum, gallium, indium, thallium, silicon, germanium, tin, lead, antimony, selenium, tellurium, polonium, neodymium, samarium, dysprosium, astatine, iron, cobalt, Raney cobalt, nickel, Raney nickel, ruthenium, rhodium, palladium, osmium, iridium, platinum, copper, silver, gold, zinc, cadmium, mercury, scandium, yttrium, lanthanum, actinium, titanium, zirconium, hafnium, vanadium, niobium, tantalum, chromium, molybdenum, tungsten, manganese, technetium, rhenium, cerium, praseodymium, WC, TiC, TaC, VC or mixtures thereof, WC-cobalt, TiC-cobalt, TaC-cobalt, VC-cobalt or mixtures thereof and also carbon and/or III) an active component selected from the group of the inorganic acids, the metals selected from among lithium, sodium, potassium, rubidium, cesium, francium, beryllium, magnesium, calcium, strontium, barium, boron, aluminum, gallium, indium, thallium, silicon, germanium, tin lead, arsenic, antimony, bismuth, selenium, tellurium, polonium, astatine, iron, cobalt, Raney cobalt, nickel, Raney nickel, ruthenium, rhodium, palladium, osmium, iridium, platinum, copper, silver, gold, zinc, cadmium, mercury, scandium, yttrium, lanthanum, actinium, titanium, zirconium, hafnium, vanadium, niobium, tantalum, chromium, molybdenum, tungsten, manganese, technetium, rhenium, cerium, praseodymium, mixtures thereof, or their borates, carbonates, silicates, nitrates, phosphates, arsenates, antimonates, bismuthates, sulfates, selenates, tellurates, vanadates, molybdates, niobates, chromates, oxides, hydroxides, halides, sulfides, selenides, tellurides, nitrides, phosphides, arsenides, acetates, acetylacetonates, palladates, platinates, cyanides, thiocyanates, manganates, rhenates, osmates, carbides, silicides, borides, their ammonium compounds or their mixtures and/or IV) an organic powder selected from the group Teflon or polyimide B) from 30 to 85% by volume of a polyethylene or polypropylene polymer or of a copolymer of ethylene, propylene, 1-butene or isobutene or of a polystyrene copolymer or of a polymethyl methacrylate copolymer or of a polyethylene oxide copolymer or of an ethylene-vinyl acetate copolymer or of a mixture of $B_1$) from 50 to 100% by weight of a polyoxymethylene homopolymer or copolymer and $B_2$) from 0 to 50% by weight of a polymer homogeneously dissolved in $B_1$) or dispersed in $B_1$) at a mean particle size of less than 1 $\mu$m and C) from 0 to 15% by volume of a dispersant, removing the binder by pyrolysis at from 400 to 600° C. and subsequent presintering at from 600 to 1400° C. and, if desired, applying active components III) to the component A) or to the presintered composition by single or multiple steeping, impregnation, spray impregnation, precipitating on, hicoating, washcoating or spray drying, wherein the catalyst support or catalyst after the pyrolytic removal of the binder has a BET specific surface area of from 0.01 to 250 $m^2$/g and a pore size distribution of from 50 to 300,000 nm measured by the mercury pressure porosimetry method, and also their use for preparing chlorine from hydrogen chloride in a non-steady-state Deacon process, for the reaction of ethylbenzene to give styrene in a non-steady-state oxydehydrogenation, for preparing aziridine from ethanolamine, for the reaction of trimethylcyclohexenone to give trimethylphenol, in reductions, hydrogenations, oxidations, dehydrogenations, acid- or base-catalyzed reactions or reactions in a fluidized bed, for removing combustion residues from diesel exhaust gases and for removing $NO_x$ from waste gases, in bioreactors together with bacteria and as biocatalyst supports with immobilized enzymes or microbes.

The catalyst supports or catalysts of the present invention are preferably not zeolitic and have a BET specific surface area of from 0.01 to 250 $m^2$/g, preferably from 0.1 to 200 $m^2$/g, particularly preferably from 0.5 to 120 $m^2$/g, and a monomodal or a polymodal, ie. a bimodal, trimodal, tetramodal or higher-modal, preferably a bimodal, trimodal or tetramodal, particularly preferably a bimodal or trimodal, pore size distribution having a mean pore diameter of from 50 to 300,000 nm, preferably from 100 to 50,000 nm, particularly preferably from 150 to 25,000 nm, measured by the mercury pressure porosimetry method and a) from 10 to 95%, preferably from 30 to 95%, particularly preferably from 50 to 95%, of the pore volume is at from 0.2 to 100 times the mean pore diameter and/or b) from 10 to 80%, preferably from 30 to 80%, particularly preferably from 50 to 80%, of the pore volume is at from 0.8 to 100 times the mean pore diameter and/or c) from 50 to 95%, preferably from 70 to 95%, particularly preferably from 80 to 95%, of the pore volume is at from 0.2 to 1 times the mean pore diameter and/or d) from 50 to 80%, preferably from 60 to 80%, particularly preferably from 65 to 80%, of the pore volume is at from 0.8 to 1 times the mean pore diameter and e) the width at half height of the pore size distribution is less than 0.6 times, ie. from 0.001 to 0.59 times, preferably from 0.005 to 0.4 times, particularly preferably from 0.1 to 0.35 times, the mean pore diameter.

Among the catalyst supports or catalyts of the present invention, preference is given to those in which the conditions a) and b) or a) and c) or a) and d) or b) and c) or b) and d) or c) and d) are simultaneously met, particular preference is given to those in which the conditions a), b) and c) or a), b) and d) or a), c) and d) or a), c) and d) or b), c) and d) are simultaneously met, particularly preferably those catalyst supports or catalysts in which all four conditions a), b), c) and d) are simultaneously met.

Figure 1:
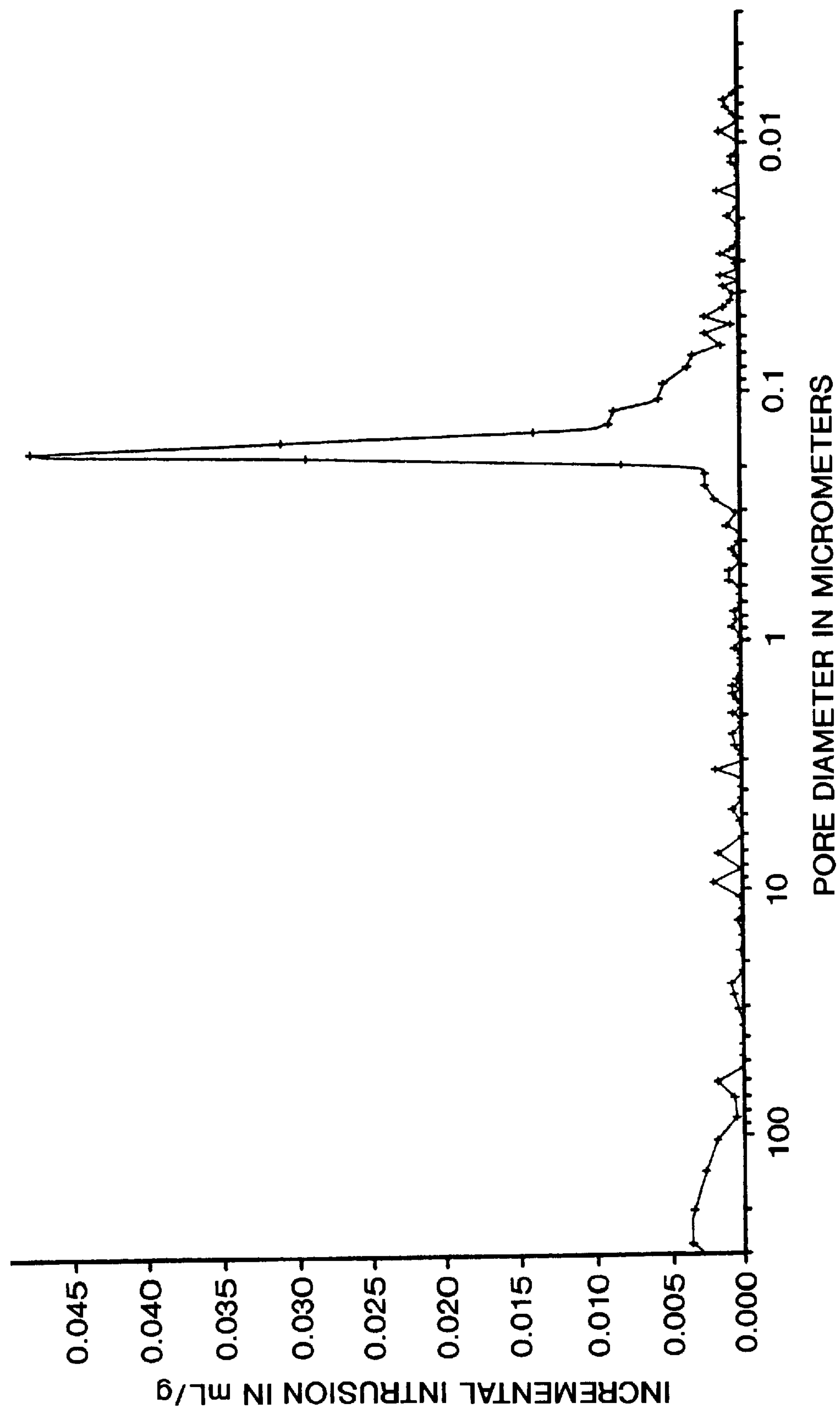
FIGS. 1–9 represent plots of the incremental intrusion vs. diameter for the composition samples defined in Table II of this specification.
Figure 2:
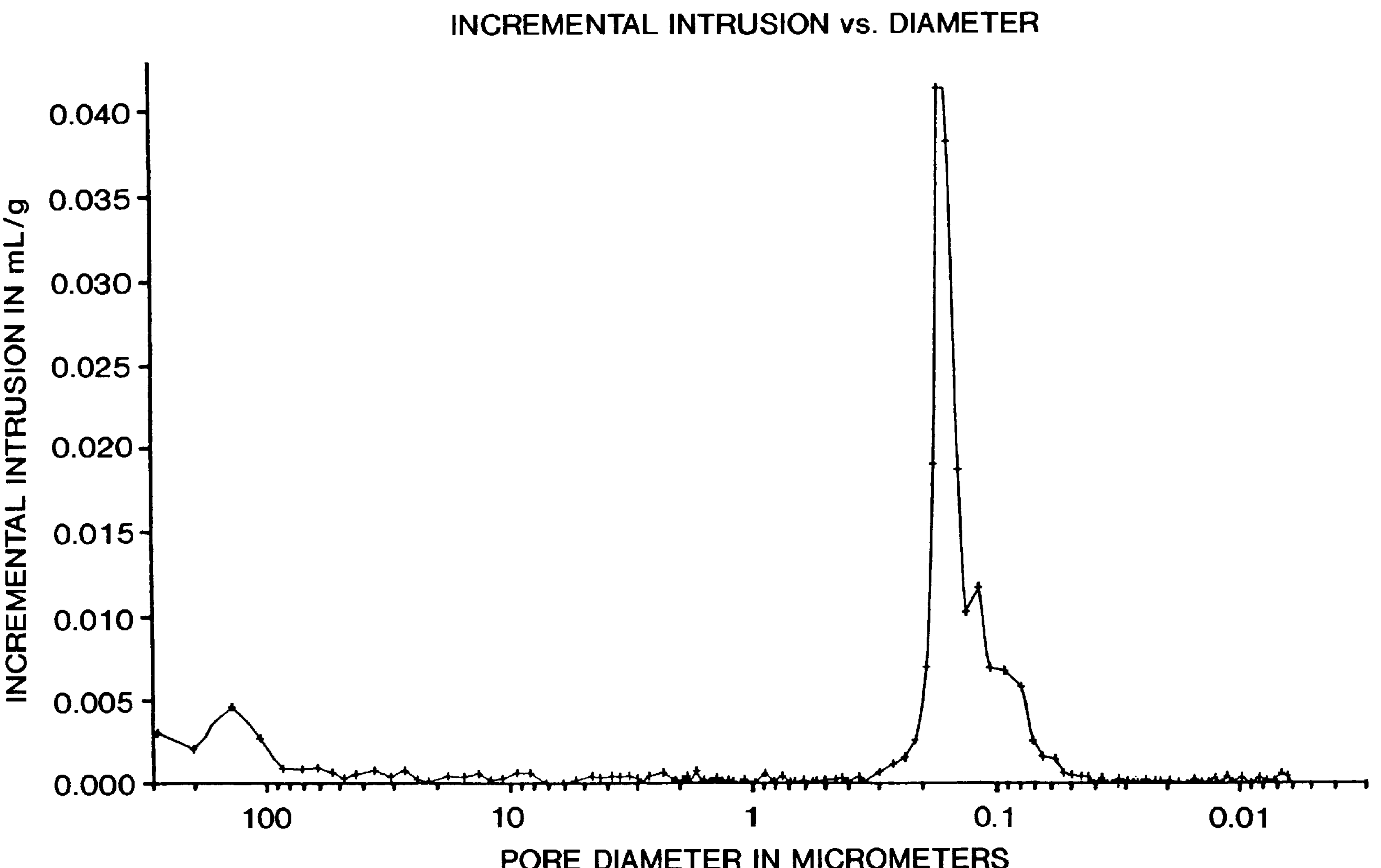
Figure 3:
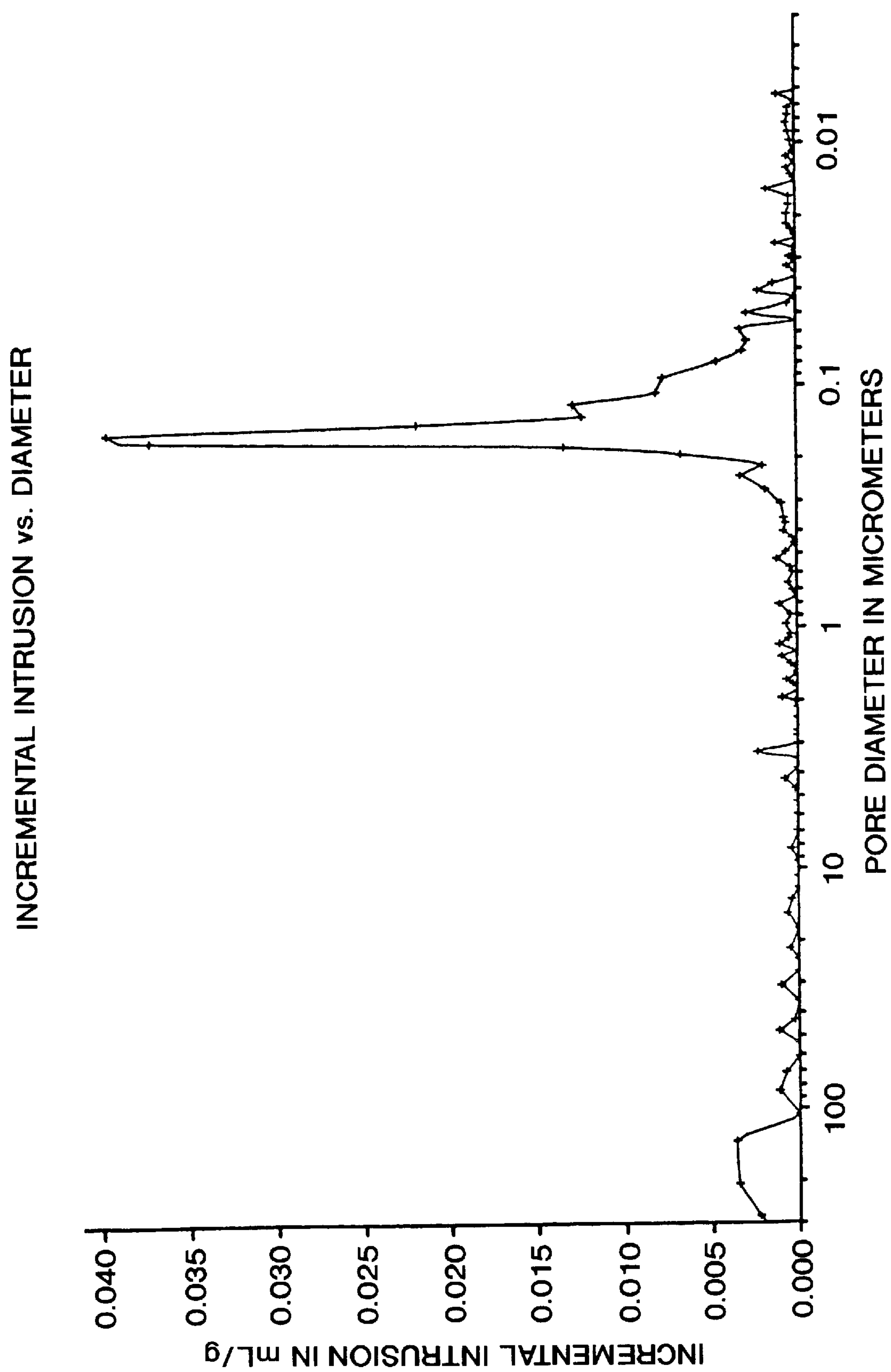
Figure 4:
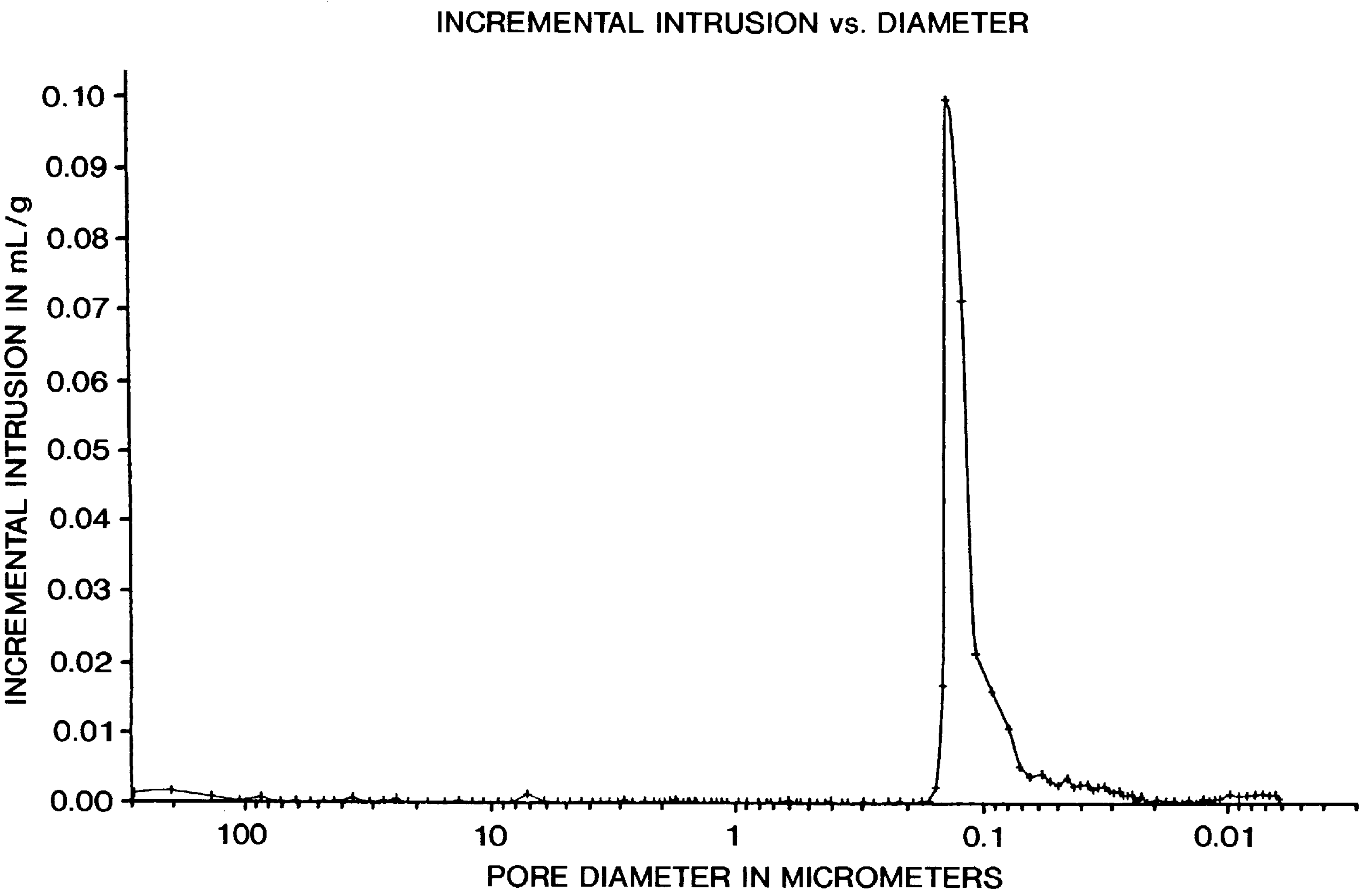
Figure 5:
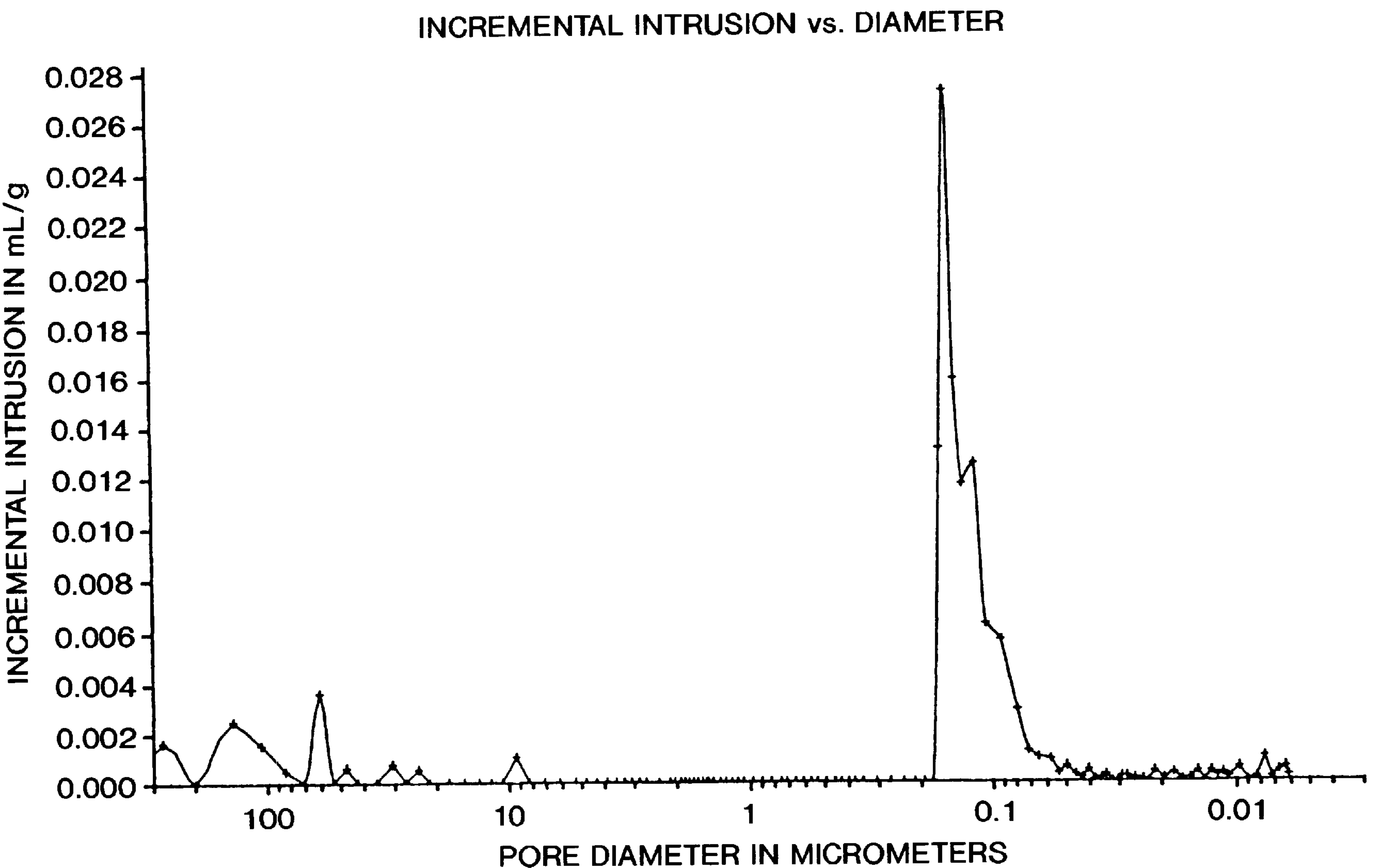
Figure 6:
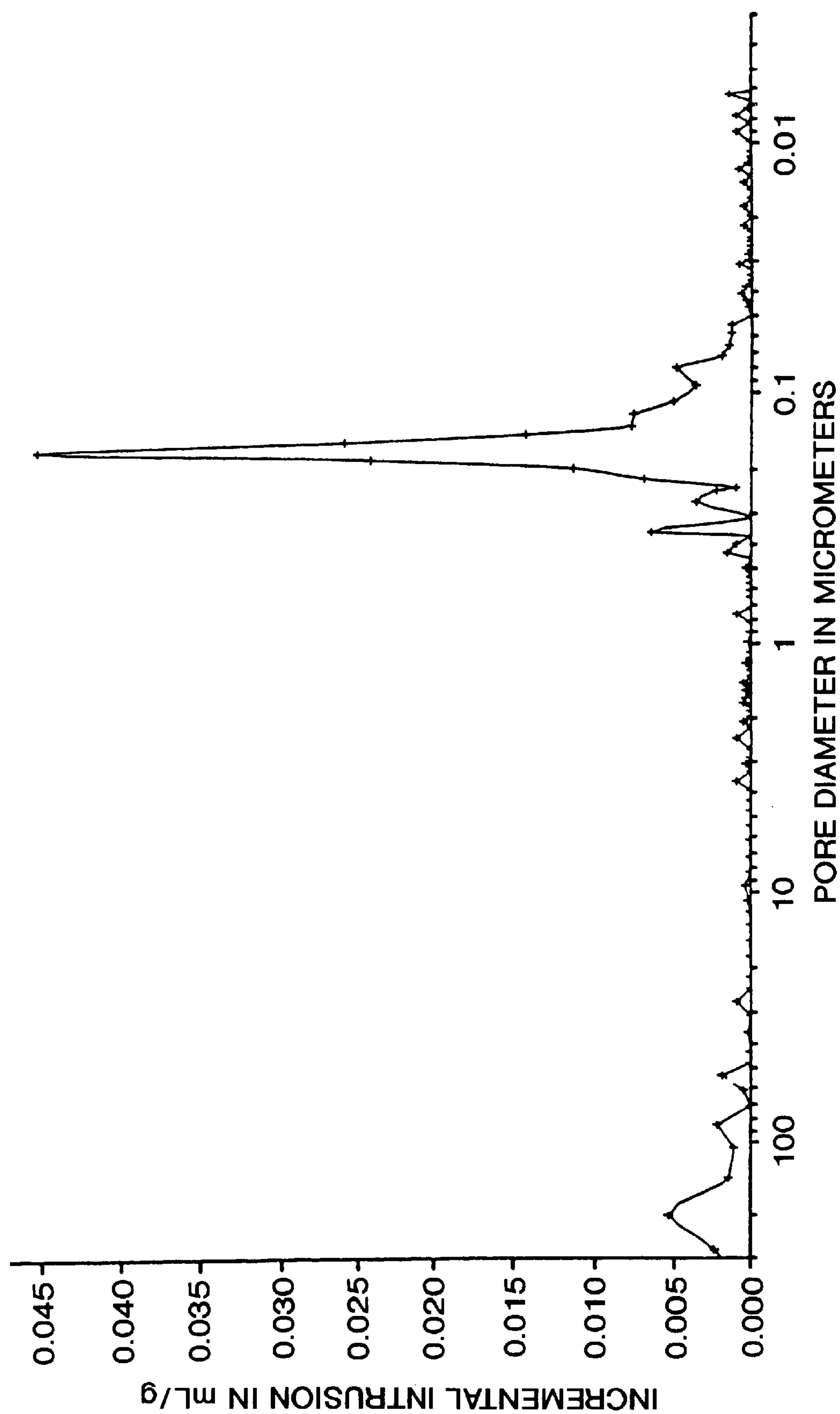
Figure 7:
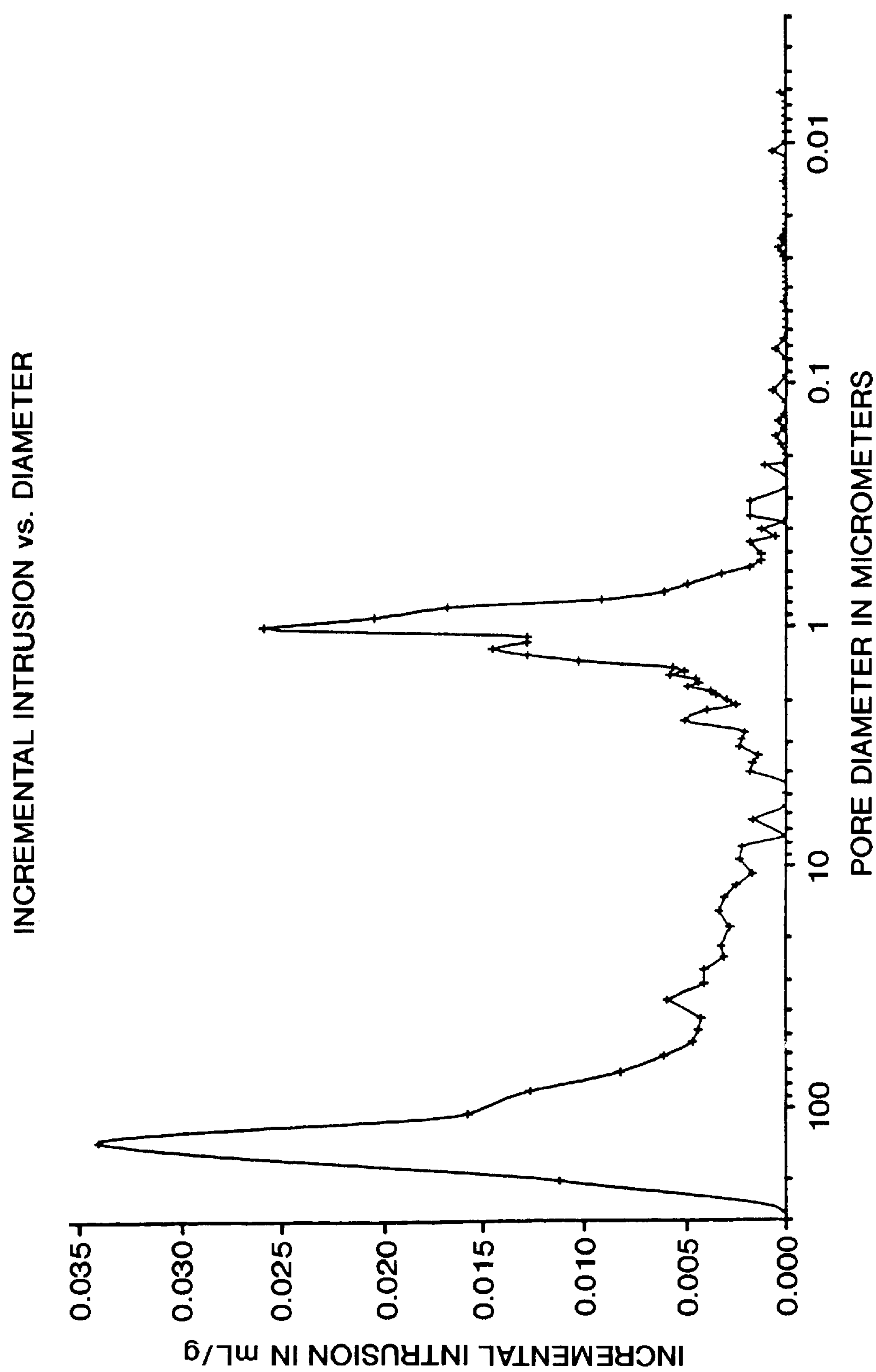
Figure 8:
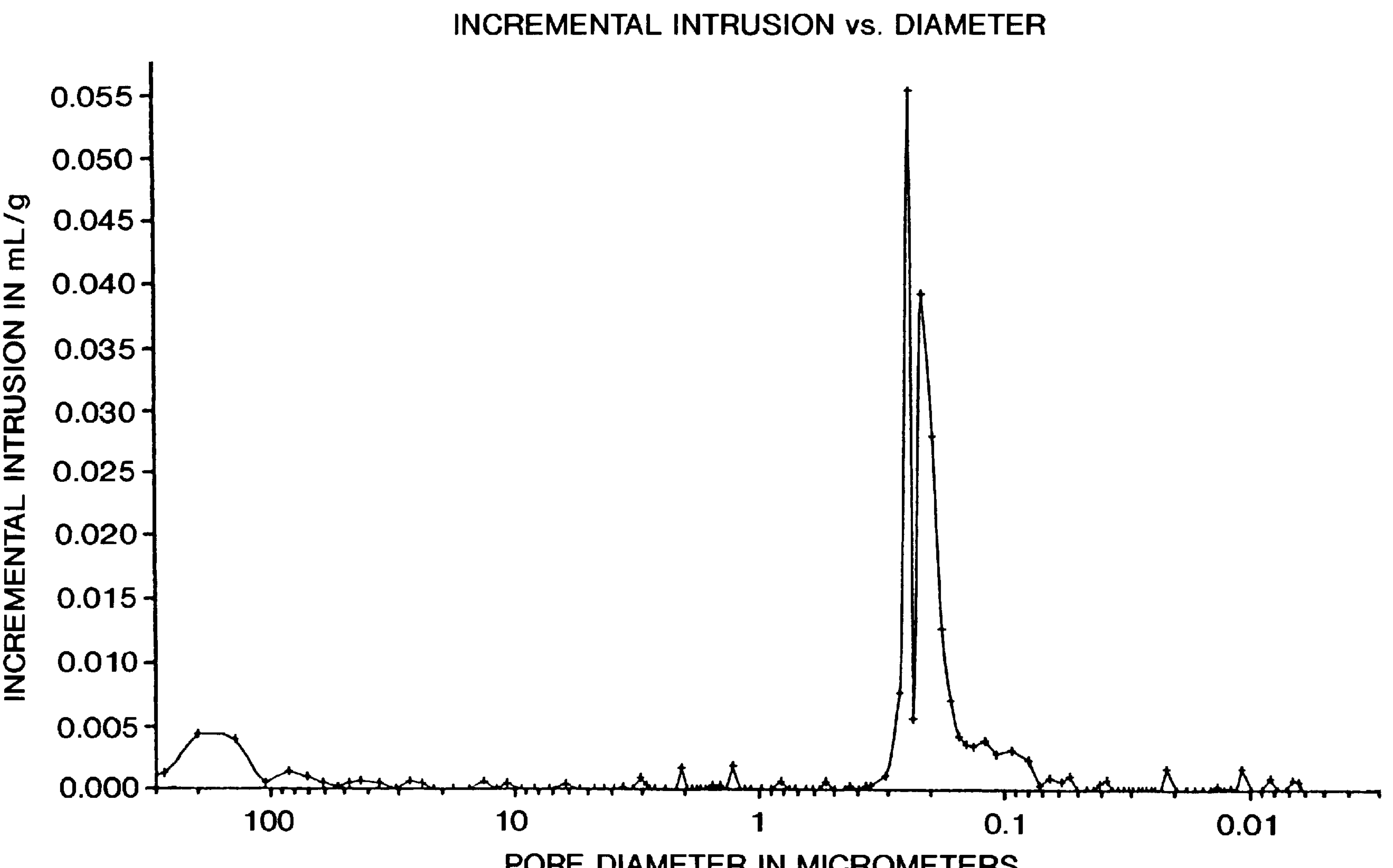

The catalyst supports or catalysts of the invention can be produced as follows:

In a mixing apparatus, preferably provided with heating, for example a kneader, an extruder or a shearing roller extruder, the component A), the inorganic, metallic, organic powders and/or the active components and then the dispersant of component C) or first component C) and then component A) or the components A) and C) together can be added to the polymer of component B) in the molten state at from 80 to 250° C., preferably from 100 to 220° C., particularly preferably from 120 to 200° C. The intimately (intensively) mixed compositions can be shaped, for example, by granulating, pressing, rolling, continuous casting, extrusion or injection molding, in particular by injection molding at from 120 to 250° C., preferably from 140 to 220° C., particularly preferably from 150 to 200° C., and pressures of from 500 to 2000 bar, preferably from 600 to 1800 bar, particularly preferably from 700 to 1600 bar. Here, in a shaping step at injection molding tool temperatures of from 40 to 160° C., preferably from 60 to 150° C., particularly preferably from 80 to 140° C., it is possible to produce catalyst supports or catalysts of any desired shape as a bed of individual parts or as monolith in the form of for example Raschig rings, saddles, star rings, perforated and/or ribbed geometric bodies such as rings, spheres, cuboids, cubes, cones, pyramids, prisms, octahedra, cylinders, truncated pyramids and truncated cones, generally without further shaping.

Wagon wheel profiles, honeycomb profiles and window frame profiles can be extruded to form monoliths at from 120 to 280° C., particularly preferably at from 180 to 200° C.

The green bodies obtained after the shaping procedure can be treated by pyrolysis at from 300 to 600° C., preferably from 350 to 600° C., particularly preferably from 400 to 600° C., and be converted by subsequent presintering, generally at from 600 to 1400° C., preferably from 600 to 1100° C., particularly preferably at from 600 to 800° C., under oxidizing conditions (air), inert gas ($N_2$, Ar, He) or reducing conditions ($N_2/H_2$, $Ar/H_2$) into the catalyst supports or catalysts having their final strength and pore distribution. The presintering process generally considerably increases the stability and the hardness of the porous shaped bodies. The cutting hardness of the specimens presintered at 800° C. is generally from 1 to 8 kg (800° C.), preferably from 1.5 to 7 kg (800° C.), particularly preferably from 2 to 6 kg (800° C.). In the case of specimens pre-sintered at 1100° C., cutting hardnesses of up to 20 kg are achieved. The water absorption is generally in the range from 0.05 to 5 ml/g, preferably from 0.1 to 3 ml/g, particularly preferably from 0.1 to 1 ml/g, so that more active component can be applied to a catalyst support of the present invention, generally without significant impairment of the hardness. By means of the calculated active component uptake, the catalysts can readily be recycled after use by reimpregnation with the active components. Besides strictly monomodal pore size distributions, it is also possible to produce polymodal (bimodal, trimodal, tetramodal and higher-modal) pore size distributions in this way. This process enables catalyst supports and catalysts having a high strength and a high thermal or chemical stability to be produced. Conceivable geometries of the shaped bodies are all shapes which can be produced by granulation, rolling, pressing, extrusion or injection molding. The shaped bodies can be used in catalytic reactions as loose material or in the form of monoliths.

The BET specific surface areas of the catalyst supports and catalysts of the present invention are generally from 0.01 to 250 $m^2/g$, preferably from 0.1 to 150 $m^2/g$, particularly preferably from 1 to 100 $m^2/g$, in particular from 2 to 8 $m^2/g$ (800° C.).

The mean pore size is generally determined by the particle size of component A), the inorganic, metallic, organic powders and/or the active components, only by means of the interstitial spaces between the powder particles used. The mean pore size and the pore size distribution therefore depend on the mean particle size and the particle size distribution of the powder used. Commercially available metal or ceramic powders enable mechanically stable, crack-free, monomodal or polymodal porous materials, such as the catalyst supports or catalysts of the present invention, to be produced in this way. The narrow pore size distribution can thus be set in the mesopore or macropore range depending on requirements and generally leads to a highly monodisperse pore distribution.

In case a polymodal catalyst support or catalyst are to be obtained, a powder having a polymodal particle size distribution or having internal porosity is used.

The mean particle size of the powder of component A) used according to the invention can generally be a nanocrystalline powder of from 5 nm to 500,000 nm, preferably from 300 nm to 100,000 nm, particularly preferably from 500 nm to 50,000 nm, with the particle size of 80%, preferably 90 %, particularly preferably 95%, of the particles deviating by from 0 to 30 %, preferably from 0 to 20%, particularly preferably from 0 to 10%, from the mean particle size.

Suitable components A) are:

I) an inorganic powder selected from the group of oxides, nitrides, carbides, silicates, aluminosilicates of the elements beryllium, magnesium, calcium, strontium, barium, boron, aluminum, gallium, indium, thallium, silicon, germanium, tin, lead, antimony, selenium, tellurium, polonium, astatine, iron, cobalt, nickel, ruthenium, rhodium, palladium, osmium, iridium, platinum, copper, silver, gold, zinc, cadmium, mercury, scandium, yttrium, lanthanum, actinium, titanium, zirconium, hafnium, vanadium, niobium, tantalum, chromium, molybdenum, tungsten, manganese, technetium, rhenium, cerium, praseodymium or their mixtures, preferably oxides, nitrides, carbides, silicates of the elements magnesium, calcium, strontium, barium, boron, aluminum, silicon, tin, lead, antimony, iron, cobalt, nickel, ruthenium, rhodium, palladium, platinum, copper, silver, gold, zinc, yttrium, lanthanum, titanium, zirconium, vanadium, niobium, tantalum, chromium, molybdenum, tungsten, manganese, cerium or their mixtures, particularly preferably oxides, nitrides, carbides of the elements magnesium, calcium, strontium, barium, boron, aluminum, silicon, tin, antimony, iron, cobalt, nickel, copper, yttrium, titanium, zirconium, vanadium, niobium, tantalum, chromium, molybdenum, tungsten, manganese or mixtures thereof, II) a metallic powder selected from among metals and alloys of the elements boron, aluminum, gallium, indium, thallium, silicon, germanium, tin, lead, antimony, selenium, tellurium, polonium, neodymium, samarium, dysprosium, astatine, iron, cobalt, Raney cobalt, nickel, Raney nickel, ruthenium, rhodium, palladium, osmium, iridium, platinum, copper, silver, gold, zinc, cadmium, mercury, scandium, yttrium, lanthanum, actinium, titanium, zirconium, hafnium, vanadium, niobium, tantalum, chromium, molybdenum, tungsten, manganese, technetium, rhenium, cerium, praseodymium, WC, TiC, TaC, VC or mixtures thereof, WC-cobalt, TiC-cobalt, TaC-cobalt, VC-cobalt or mixtures thereof and also carbon, preferably metals and alloys of the elements boron, aluminum, silicon, tin, lead, antimony, selenium, neodymium, samarium, dysprosium, iron, cobalt, Raney cobalt, nickel, Raney nickel, palladium, platinum, copper, silver, gold, zinc, yttrium, lanthanum, titanium, zirconium, vanadium, niobium, tantalum, chromium, molybdenum, tungsten, manganese, cerium, WC, TiC, TaC, VC or mixtures thereof, WC-cobalt, TiC-cobalt, TaC- cobalt, VC-cobalt or mixtures thereof and also carbon, particularly preferably metals and alloys of the elements boron, aluminum, silicon, tin, neodymium, samarium, dysprosium, iron, cobalt, Raney cobalt, nickel, Raney nickel, copper, zinc, yttrium, titanium, zirconium, vanadium, niobium, tantalum, chromium, molybdenum, tungsten, manganese, WC, TiC, TaC, VC or mixtures thereof, WC-cobalt, TiC-cobalt, TaC-cobalt, VC-cobalt or mixtures thereof, III) an active component selected from the group of the inorganic acids, in particular $H_2SO_4$, $H_3PO_4$, $HNO_3$ and heteropolyacids, the metals selected from among lithium, sodium, potassium, rubidium, cesium, francium, beryllium, magnesium, calcium, strontium, barium, boron, aluminum, gallium, indium, thallium, silicon, germanium, tin, lead, arsenic, antimony, bismuth, selenium, tellurium, polonium, astatine, iron, cobalt, Raney cobalt, nickel, Raney nickel, ruthenium, rhodium, palladium, osmium, iridium, platinum, copper, silver, gold, zinc, cadmium, mercury, scandium, yttrium, lanthanum, actinium, titanium, zirconium, hafnium, vanadium, niobium, tantalum, chromium, molybdenum, tungsten, manganese, technetium, rhenium, cerium, praseodymium, their mixtures or their borates, carbonates, silicates, nitrates, phosphates, arsenates, antimonates, bismuthates, sulfates, selenates, tellurates, vanadates, molybdates, niobates, chromates, oxides, hydroxides, halides, sulfides, selenides, tellurides, nitrides, phosphides, arsenides, acetates, acetylacetonates, palladates, platinates, cyanides, thiocyanates, manganates, rhenates, osmates, carbides, silicides, borides, their ammonium compounds or their mixtures, preferably metals selected from among lithium, sodium, potassium, cesium, magnesium, calcium, strontium, barium, boron, aluminum, silicon, tin, lead, arsenic, antimony, bismuth, selenium, tellurium, polonium, iron, cobalt, Raney cobalt, nickel, Raney nickel, ruthenium, rhodium, palladium, osmium, iridium, platinum, copper, silver, gold, zinc, yttrium, lanthanum, titanium, zirconium, vanadium, niobium, tantalum, chromium, molybdenum, tungsten, manganese, rhenium, cerium, their mixtures or their borates, carbonates, silicates, nitrates, phosphates, arsenates, antimonates, bismuthates, sulfates, selenates, vanadates, molybdates, niobates, chromates, oxides, hydroxides, halides, sulfides, selenides, tellurides, nitrides, phosphides, arsenides, acetates, acetylacetonates, palladates, platinates, manganates, carbides, silicides, borides, their ammonium compounds or their mixtures, particularly preferably metals selected from among lithium, sodium, potassium, cesium, magnesium, calcium, strontium, barium, aluminum, silicon, tin, lead, arsenic, antimony, bismuth, iron, cobalt, nickel, ruthenium, rhodium, palladium, platinum, copper, silver, zinc, titanium, zirconium, vanadium, niobium, tantalum, chromium, molybdenum, tungsten, manganese, cerium, their mixtures or their carbonates, silicates, nitrates, phosphates, arsenates, antimonates, bismuthates, sulfates, vanadates, molybdates, niobates, chromates, oxides, hydroxides, halides, sulfides, nitrides, carbides, their ammonium compounds or their mixtures.

Preferably, as metals one selected from the group of aluminium, iron, cobalt, nickel, palladium, platinum, copper, silver, molybdenum, zinc, titanium, zirconium, tungsten, niobium, chromium and carbon, as inorganic powder one selected from the group of $Al_2O_3$, MgO, $SiO_2$, $TiO_2$, $Y_2O_3$, $ZrO_2$, ZnO, $Fe_3O_4$, $Fe_2O_3$, CoO, $Co_2O_3$, $Cr_2O_3$, NiO, $B_2O_3$, $Ce_2O_3$, $CeO_2$, $Pr_2O_3$, $B_4C$, SiC, WC, TiC, TaC, $Si_3N_4$, AlN, BN, TiN and ZrN, or a mixture of two or more thereof, more preferably, as metals one selected from the group of iron, cobalt, nickel, chromium, molybdenum and titanium, as inorganic powder one selected from the group of SiC, $Si_3N_4$, BN, $B_4C$, WC, TiC, TiN, ZrN and AlN, or a mixture of two or more thereof, and in particular as inorganic powder SiC, $Si_3N_4$ or a mixture thereof are used.

If unsupported catalysts are to be produced, the component A) consists only of active components III) and, if desired, IV), an organic powder selected from the group Teflon or polyimide.

Suitable components B) are:

Polyethylene or polypropylene polymers or copolymers of ethylene, propylene, 1-butene or isobutene or polystyrene copolymers or polymethyl methacrylate copolymers or polyethylene oxide copolymers or ethylene-vinyl acetate copolymers or mixtures of $B_1$) from 50 to 100% by weight, preferably from 70 to 90% by weight, particularly preferably from 80 to 88% by weight, of a polyoxymethylene homopolymer or copolymer as is known from EP-A-444 475 and $B_2$) from 0 to 50% by weight, preferably from 10 to 30% by weight, particularly preferably from 12 to 25% by weight, of a mean particle size of less than 1 $\mu$m, preferably poly-1,3-dioxolane, poly-1,3-dioxane, poly-1,3-dioxepane, particularly preferably poly-1,3-dioxepane.

The organic binder can also comprise mixtures of one or more thermoplastic resins such as polyacetal, polyethylene, polypropylene, polystyrene, polymethyl methacrylate and one or more plasticizers such as polyethylene glycol, polypropylene glycol, polybutanediol formal, phthalic esters, ethylene-vinyl acetate copolymers and montan ester waxes.

Suitable polyacetal binders are, for example, polyoxymethylene which advantageously has a molecular weight of from 10,000 to 500,000. Apart from homopolymers of formaldehyde or trioxane, other suitable binders are copolymers of trioxane with, for example, cyclic ethers such as ethylene oxide and 1,3-dioxolane or formals such as 1,3-dioxepane, 1,3-dioxane, or mixtures thereof, or homopolymeric poly-1,3-dioxolane, poly-1,3-dioxane, or poly-1,3-dioxepane, with the amounts of the copolymers generally being from 10 to 30% by weight of the polymers.

In addition, they can contain auxiliaries such as thermoplastic binders such as polyethylene, polymethyl methacrylate or polyethylene oxide and dispersants or lubricants such as polyethylene glycol, stearic acid, fatty alcohols, polyvinylpyrrolidine or polyvinyl alcohol. The amount of auxiliaries is generally from 0.1 to 12% by weight of the total mass.

Suitable components C) are dispersants as are known from EP-A-444 475, for example organic carboxylic acids, amines, amides or maleimides, stearic acid, polyvinylpyrrolidone, polyvinyl alcohol, polyethylene glycol, polypropylene glycol, polyethylene oxide and montan waxes, preferably organic carboxylic acids, amines, amides or maleimides, polyethylene glycol and carboxylic acids, amines, amides or maleimides, polyethylene glycol and polyethylene oxide, particularly preferably organic carboxylic acids, amines, maleimides, polyethylene glycol and polyethylene oxide.

The mixtures used for producing (mixing together) the catalyst supports or catalysts of the present invention generally comprise or consist of from 15 to 70% by weight, preferably from 30 to 70% by weight, particularly preferably from 50 to 65% by weight, of component A), from 30 to 85 % by weight, preferably from 30 to 70% by weight, particularly preferably from 35 to 50% by weight, of component B) and from 0 to 15% by weight, preferably from 1 to 12% by weight, particularly preferably from 2 to 8% by weight, of component C).

Suitable support materials are ceramic, metallic or organic powders of A I, II and IV.

In the case of the unsupported catalyst, the active components can be used directly as powder or in the case of supported catalysts they can be applied to the inorganic powder I), the metallic powder II), the organic powder IV) or mixtures thereof, or subsequently to the support material, or can be compounded together with the support material.

Furthermore, inorganic or organic fibers or whiskers of, for example, $Al_2O_3$, $SiO_2$, SiC, $Si_3N_4$, C or mixtures thereof can be added to the compositions.

In the preparative process of the present invention, the components A) are generally deagglomerated with the aid of a dispersant C) and the thus uniformly sized starting powder particles are incorporated at a comparatively high component A) content into an organic binder [component B)]. The organic binder fills the generally almost uniformly sized and regularly arranged interstitial spaces between the powder particles. The macropores in the range around 100 $\mu$m present in the starting powder of the component A) as a result of agglomerate formation are generally eliminated by the deagglomeration. Removal of the organic binder and the organic dispersant leaves, when powders having a narrow monomodal particle size distribution are used, very uniformly sized pores between the powder particles. In general, the mean pore diameter is 25% of the mean particle diameter of the powder used (see table [unit: dm/kg]). When using powders having a polymodal particle size distribution or when using porous powders, polymodal (bimodal, trimodal, tetramodal or higher-modal) pore distributions can also be produced, with the pore size being determined by the interstitial spaces between the powder particles and by the internal porosity of the powder particles.

The catalysts of the present invention can be heterogeneous supported catalysts or unsupported catalysts. Unsupported catalysts consist of catalytically active material. Supported catalysts can be produced by coating inert porous ceramic or metallic catalyst supports with catalytically active components or precursors of catalytically active components by steeping, impregnation, spray impregnation, spray drying, precipitating on, hicoating, washcoating.

Thus, the invention also relates to a monomodal or polymodal catalyst support or catalyst, obtainable by shaping a mixture of A) from 15 to 70% by volume of I) an inorganic powder selected from the group of oxides, nitrides, carbides, silicates, aluminosilicates of the elements beryllium, magnesium, calcium, strontium, barium, boron, aluminum, gallium, indium, thallium, silicon, germanium, tin, lead, antimony, selenium, tellurium, polonium, astatine, iron, cobalt, nickel, ruthenium, rhodium, palladium, osmium, iridium, platinum, copper, silver, gold, zinc, cadmium, mercury, scandium, yttrium, lanthanum, actinium, titanium, zirconium, hafnium, vanadinium, niobium, tantalum, chromium, molybdenum, tungsten, manganese, technetium, rhenium, cerium, praseodymium or mixtures thereof and/or II) a metallic powder selected from among metals and alloys of the elements boron, aluminum, gallium, indium, thallium, silicon, germanium, tin, lead, antimony, selenium, tellurium, polonium, neodymium, samarium, dysprosium, astatine, iron, cobalt, Raney cobalt, nickel, Raney nickel, ruthenium, rhodium, palladium, osmium, iridium, platinum, copper, silver, gold, zinc, cadmium, mercury, scandium, yttrium, lanthanum, actinium, titanium, zirconium, hafnium, vanadinium, niobium, tantalum, chromium, molybdenum, tungsten, manganese, technetium, rhenium, cerium, praseodymium, WC, TiC, TaC, VC or mixtures thereof, WC-cobalt, TiC-cobalt, TaC-cobalt, VC-cobalt or mixtures thereof and also carbon and/or III) an active component selected from the group of the inorganic acids, the metals selected from among lithium, sodium, potassium, rubidium, cesium, francium, beryllium, magnesium, calcium, strontium, barium, boron, aluminum, gallium, indium, thallium, silicon, germanium, tin, lead, arsenic, antimony, bismuth, selenium, tellurium, polonium, astatine, iron, cobalt, Raney cobalt, nickel, Raney nickel, ruthenium, rhodium, palladium, osmium, iridium, platinum, copper, silver, gold, zinc, cadmium, mercury, scandium, yttrium, lanthanum, actinium, titanium, zirconium, hafnium, vanadinium, niobium, tantalum, chromium, molybdenum, tungsten, manganese, technetium, rhenium, cerium, praseodymium, mixtures thereof, or their borates, carbonates, silicates, nitrates, phosphates, arsenates, antimonates, bismuthates, sulfates, selenates, tellurates, vanadates, molybdates, niobates, chromates, oxides, hydroxides, halides, sulfides, selenides, tellurides, nitrides, phosphides, arsenides, acetates, acetylacetonates, palladates, platinates, cyanides, thiocyanates, manganates, rhenates, osmates, carbides, silicides, borides, their ammonium compounds or their mixtures and/or IV) an organic powder selected from the group Teflon or polyimide B) from 30 to 85% by volume of a polyethylene or polypropylene polymer or of a copolymer of ethylene, propylene, 1-butene or isobutene or of a polystyrene copolymer or of a polymethyl methacrylate copolymer or of a polyethylene oxide copolymer or of an ethylene-vinyl acetate copolymer or of a mixture of $B_1$) from 50 to 100% by weight of a polyoxymethylene homopolymer or copolymer and $B_2$) from 0 to 50% by weight of a polymer homogeneously dissolved in $B_1$) or dispersed in $B_1$) at a mean particle size of less than 1 $\mu$m and C) from 0 to 15% by volume of a dispersant, removing the binder by pyrolysis at from 300 to 600° C. and subsequent presintering at from 600 to 1400° C. and, if desired, applying active components III to the component A) or to the presintered composition by single or multiple steeping, impregnation, spray impregnation, precipitating on, hicoating, washcoating or spray drying, wherein the catalyst support or catalyst after the pyrolytic removal of the binder has a BET specific surface area of from 0.01 to 250 $m^2/g$ and a pore size distribution of from 50 to 300,000 m measured by the mercury pressure porosimetry method.

The catalyst supports or catalysts of the present invention are, in general, suitable for use in:

reductions (hydrogenations), for example: hydrogenation of alkynes, for example the selective hydrogenation of acetylene in $C_2$, $C_3$, $C_4$ mixtures, the selective hydrogenation of vinylacetylenes in $C_4$ fractions and the hydrogenation of butynediol to give butenediol or butanediol, the hydrogenation of alkenes, for example the hydrogenation of unsaturated compounds in the oxo process, aminative hydrogenation, hydrogenation of aromatics, diolefin hydrogenation such as the hydrogenation of diolefins in pyrolysis gasoline, fat hydrogenation, hydrogenative desulfurization such as the hydrogenation of inorganic sulfur compounds, eg. COS, $CS_2$, $SO_2$ and $S_x$, to give hydrogen sulfide, hydrogenative refining of aromatics or paraffins, the hydrogenation of organic chlorine compounds, the hydrogenation of aldehydes, carboxylic acids, carboxylic esters, ketones, nitrites, nitro compounds, oximes and oxo products, for example the reduction of nitrobenzene to give aniline, the hydrogenation of carbonyl groups and aromatics, eg. for producing white oil, the hydrogenation of trimethylquinone to give trimethylhydroquinone, the hydrogenation of adiponitrile to give hexamethylenediamine, acrylonitrile, $NH_3$ and the hydrogenation of adipic acid to give hexanediol, the hydrogenation of cyclohexyl hydroperoxide to give cyclohexanol, the hydrogenation of citral to give citronellal, the preparation of lilial from dehydrolilial, the removal of $NO_x$ from waste gases by reduction with ammonia or alkanes and the preparation of alkanes, olefins, alcohols, aldehydes and/or carboxylic acids from synthesis gas, the hydrogenation of adiponitrile to give aminocapronitrile, the aminative hydrogenation of adipic acid to give aminocapronitrile;

oxidations (dehydrogenations), for example: oxidations of alkanes such as the dehydrogenation of ethylbenzene to give styrene or of dimethylcyclohexylamine to give 2,6-dimethylaniline, of alkenes, of alcohols, for example the dehydrogenation of cyclohexanol to give cyclohexanone and the preparation of ethylhexanoic acid and ethylhexanal from ethylhexenol, ammonoxidation such as the preparation of hydrogen cyanide from methane or of o-xylene to give phthalodinitrile, of aromatics, epoxidation, oxidative halogenation, oxidative coupling, oxidation of hydrogen sulfide-containing gases to sulfur by the Claus process, the preparation of vinyl chloride by the oxychlorination process (Stauffer process), the oxidation of hydrogen sulfide and/or organic sulfur compounds to sulfur dioxide, the preparation of sulfuric acid by the contact process from $SO_2$-containing gases, the preparation of phthalic anhydride from o-xylene and air, the catalytic combustion of hydrocarbons, solvents or CO-contaminated waste gas, the preparation of ethylene dichloride by oxychlorination of ethylene, the oxidation of propene to give acrylic acid, the preparation of methacrylic acid from methacrolein, the preparation of methacrylic acid from isobutyric acid, the dehydrogenation of DMCHA to give xylidine and the dehydrogenation of trimethylcyclohexenone to give trimethylphenol, the oxidation of ethylene to ethylene oxide, the oxidation of butadiene to furan, the oxidation of propene to acrolein, the oxidation of acrolein to acrylic acid, the oxidation of methacrolein to methacrylic acid;

acid- or base-catalyzed reactions, for example: alkoxylations, eg. of ethylene oxide or propylene oxide, dealkoxylations, eg. of N-vinylformamide from $\alpha$-methoxyethylformamide, alkylations, acylations, hydrations, dehydrations, eg. of aziridine from ethanolamine or of hydrocyanic acid from formamide, aminations, aldol reactions, oligomerizations, polymerizations, polymer-analogous reactions, cyclizations, isomerizations, esterifications, cracking of gaseous hydrocarbons, eg. of natural gas using steam and possibly $CO_2$, the oxidation of propene to acrolein, elimination reactions such as N-formylalanine nitrile to give N-vinylformamide, additions such as methanol or propyne to $\alpha$-methoxy groups.

Also suitable are macroporous supports having a pore size from 100 to 10,000 nm for removing combustion residues (soot) from diesel exhausts and for bioreactors in combination with the use of bacteria (from 1 to 2 $\mu$m).

The catalyst supports or catalysts produced by the process of the present invention have comparatively high mechanical strengths and are therefore particularly suitable for fluidized bed reactions.

Fluidized bed reactions can be used, for example, for the rearrangement of cyclohexanoneoxime to give $\epsilon$-caprolactam, the ammonoxidations of, for example, toluene to give benzonitrile or of propene to give acrylonitrile, the preparation of maleic anhydride from butene or the preparation of aniline from nitrobenzene.

Thus, the present invention also relates to a method of preparing chlorine from hydrogen chloride in a non-steady-state Deacon process by using the monomodal or polymodal catalyst support or catalyst, a method of reacting ethyl benzine to give styrene in a non-steady-state oxydehydrogenation by using the monomodal or polymodal catalyst support or catalyst, a method of preparing aziridine form ethanol amine by using the monomodal or polymodal catalyst support or catalyst, a method of reaction trimethyl cyclohexenon to give trimethylphenol by using the monomodal or polymodal catalyst support or catalyst, a method of reduction by using the monomodal or polymodal catalyst support or catalyst, a method of hydrogenating by using the monomodal or polymodal catalyst support or catalyst, a method of oxidizing by using the monomodal or polymodal catalyst support or catalyst, a method of dehydrogenating by using the monomodal or polymodal catalyst support or catalyst, a method of carrying out acid- or base-catalyzed reactions by using the monomodal or polymodal catalyst support or catalyst, a method of carrying out fluidized bed by using the monomodal or polymodal catalyst support or catalyst, a method of removing combustion residues from diesel exhaust gases by using the monomodal or polymodal catalyst support or catalyst, a method of removing $NO_x$ from waste gases by using the monomodal or polymodal catalyst support or catalyst, a method of carrying out reactions in bioreactors in the presence of bacteria by using the monomodal or polymodal catalyst support or catalyst, and a method of carrying out reactions in the presence of a biocatalyst by using the monomodal or polymodal catalyst support as a catalyst support with immobilized enzymes or microbes.

The invention also relates to a method of preparing chlorine from hydrogen chloride in a non-steady-state Deacon process by using the monomodal or polymodal catalyst support or catalyst,

- a method of reacting ethyl benzene to give styrene in a non-steady-state oxy dehydrogenation by using the monomodal or polymodal catalyst support or catalyst,
- a method of preparing aziridine form ethanol amine by using the monomodal or polymodal catalyst support or catalyst,
- a method of reacting trimethyl cyclohexenon to give trimethylphenol by using the monomodal or polymodal catalyst support or catalyst,
- a method of reducing by using the monomodal or polymodal catalyst support or catalyst,
- a method of hydrogenating by using the monomodal or polymodal catalyst support or catalyst,
- a method of oxidizing by using the monomodal or polymodal catalyst support or catalyst,
- a method of dehydrogenating by using the monomodal or polymodal catalyst support or catalyst,
- a method of carrying out acid- or base-catalyzed reactions by using the monomodal or polymodal catalyst support or catalyst,
- a method of carrying out fluidized bed reactions by using the monomodal or polymodal catalyst support or catalyst,
- a method of removing combustion residues from diesel exhaust gases by using the monomodal or polymodal catalyst support or catalyst,
- a method of removing $NO_x$ from waste gases by using the monomodal or polymodal catalyst support or catalyst,
- a method of carrying out reactions in bioreactors in the presence of bacteria by using the monomodal or polymodal catalyst support or catalyst,
- a method of carrying out reactions in the presence of a biocatalyst by using the monomodal or polymodal catalyst support as a catalyst support with immobilized enzymes or microbes.

In the above, the catalyst support or catalyst referred to is the catalyst support or catalyst of the present invention.

EXAMPLES

Example 1

The ceramic powder 1 from Table I was kneaded at 180° C. with a binder based on polyacetal, comprising a polyoxymethylene copolymer (POM/PBDF) of trioxane and 2.5% by weight of butanediol formal having an average molecular weight of 150,000, and with 20% by weight of polybutanediol formal having a molecular weight of 50,000 and 5% by weight (based on the powder used) of polyethylene glycol having a molecular weight of 800 as auxiliary, extruded at 180° C. to give extrudates having a diameter of 4 mm which were pyrolyzed at 600° C. for 1 hour under $N_2$ and then presintered at various temperatures in air in a muffle furnace. The process parameters are shown in Table II, the pore radius distributions and further properties of the extrudates are shown in Tables IIIa and b.

Example 2

The ceramic powder 2 from Table I was compounded at 220° C. in a double-sigma kneader with addition of polyethylene having a molecular weight of 150,000 and a density of 0.95 g/ml and polyethylene oxide having a molecular weight of 400. The feedstock was granulated via a discharge screw. The granules were pyrolyzed at 600° C. for 1 hour under $N_2$ and then presintered in air at 800° C. for 2 hours in a muffle furnace. The process parameters are shown in Table II, the pore radius distributions and further properties of the extrudates are shown in Tables IIIa and b.

Example 3

The ceramic powder 3 from Table I was compounded at 200° C. in a double-sigma kneader with addition of polystyrene having a molecular weight of 100,000 and a density of 1.04 g/ml and polyethylene oxide having a molecular weight of 400. The feedstock was granulated via a discharge screw. The granules were pyrolyzed at 500° C. for 0.5 hour under $N_2$ and then presintered at 800° C. for 0.5 hour under 50 l/h of air in a rotary tube furnace. The process parameters are shown in Table II, the pore radius distributions and further properties of the extrudates are shown in Tables IIIa and b.

Example 4

The ceramic powder 4 from Table I was compounded at 200° C. in a double-sigma kneader with 90% by weight of $Si_3N_4$ (HC STARCK, LC12) and 5% by weight of $Y_2O_3$ (HC STARCK, grade fine) and 5% by weight of $Al_2O_3$ (ALCOA, CT3000SG) with addition of polymethyl methacrylate having a molecular weight of 150,000 and a density of 1.17 g/ml and polyethylene oxide having a molecular weight of 400. The feedstock was granulated via a discharge screw. The granules were pyrolyzed at 600° C. for 1 hour under $N_2$ and then presintered in air at 600° C. for 2 hours in a muffle furnace. The process parameters are shown in Table II, the pore radius distributions and further properties of the extrudates are shown in Tables IIIa and b.

Example 5

The ceramic powder 5 from Table I was kneaded at 180° C. with a binder based on polyacetal, comprising a polyoxymethylene copolymer (POM/PBDF) of trioxane and 2.5% by weight of butanediol formal having an average molecular weight of 150,000, and with 20% by weight of polybutanediol formal having a molecular weight of 50,000 and 5% by weight (based on the powder used) of polyethylene glycol having a molecular weight of 800 as auxiliary, extruded at 180° C. to give extrudates having a diameter of 4 mm which were pyrolyzed at 600° C. under $N_2$ and then presintered at 800° C. for 2 hours in a muffle furnace. The process parameters are shown in Table II, the pore radius distributions and further properties of the extrudates are shown in Tables IIIa and b.

Example 6

The ceramic powder 6 from Table I was kneaded at 180° C. with a binder based on polyacetal, comprising a polyoxymethylene copolymer (POM/PBDF) of trioxane and 2.5% by weight of butanediol formal having an average molecular weight of 150,000, and with 20% by weight of polybutanediol formal having a molecular weight of 50,000 and 5% by weight (based on the powder used) of polyethylene glycol having a molecular weight of 800 as auxiliary, extruded at 180° C. to give extrudates having a diameter of 4 mm which were first pyrolyzed under nitrogen at 600° C. for 1 hour in a muffle furnace and then presintered in air at 1100° C. for 2 hours. The process parameters are shown in Table II, the pore radius distributions and further properties of the extrudates are shown in Tables IIIa and b.

Example 7

The ceramic powder 7 from Table I having a bimodal particle size distribution with maxima at 1 μm was kneaded at 180° C. with a binder based on polyacetal, comprising a polyoxymethylene copolymer (POM/PBDF) of trioxane and 2.5% by weight of butanediol formal having an average molecular weight of 150,000, and with 20% by weight of polybutanediol formal having a molecular weight of 50,000 and 5% by weight (based on the powder used) of polyethylene glycol having a molecular weight of 800 as auxiliary, extruded at 180° C. to give extrudates having a diameter of 4 mm which were pyrolyzed under nitrogen at 600° C. for 1 hour in a muffle furnace and then presintered in air at 800° C. for 2 hours. The process parameters are shown in Table II, the pore radius distributions and further properties of the extrudates are shown in Tables IIIa and b.

Example 8

The ceramic powder 8 from Table I having a bimodal particle size distribution with maxima at 1 μm was kneaded at 180° C. with a binder based on polyacetal, comprising a polyoxymethylene copolymer (POM/PBDF) of trioxane and 2.5% by weight of butanediol formal having an average molecular weight of 150,000, and with 20% by weight of polybutanediol formal having a molecular weight of 50,000 and 5% by weight (based on the powder used) of polyethylene glycol having a molecular weight of 800 as auxiliary. The cooled product was granulated in a cutter mill. The granules were pyrolyzed under nitrogen at 600° C. for 1 hour and then presintered in air at 1100° C. for 2 hours. The process parameters are shown in Table II, the pore radius distributions and further properties of the extrudates are shown in Tables IIIa and b.

TABLE I

| Ex. No. | Powder | Descreiption | Powder content vol. % | Amount of powder [g] | Polyacetal [g] | PBDF [g] | PE [g] | PMMA [g] | PS [g] | PEG [g] | PEO [g] |
|---|---|---|---|---|---|---|---|---|---|---|---|
| 1 | $Al_2O_3$ | ALCOA CT3000SG | 56 | 1000 | 162 | 41 | | | | 50 | |
| 2 | $Al_2O_3$ | ALCOA CT3000SG | 56 | 1000 | | | 169 | | | | 20 |
| 3 | $Al_2O_3$ | ALCOA CT3000SG | 56 | 1000 | | | | | 185 | | 20 |
| 4 | 90% $Si_3N_4$ | HC STARCK LC12 | 50 | 900 | | | | 334 | | | 20 |
| | 5% $Y_2O_3$ | HC STARCK grade fine | — | 50 | — | — | — | — | — | — | — |
| | 5% $Al_2O_3$ | ALCOA CT3000SG | — | 50 | — | — | — | — | — | — | — |
| 5 | $ZrO_2$ | TOSOH TZ-3YS | 50 | 1000 | 127 | 32 | | | | 50 | |
| 6 | $Al_2O_3$ | ALCOA CT3000SG | 56 | 1000 | 162 | 41 | | | | 50 | |
| 7 | $Al_2O_3$ | ALCOA tabular | 50 | 1000 | 219 | 55 | | | | 50 | |
| 8 | $Al_2O_3$ | Norton, FCP13N-LC | 49 | 1000 | 295 | 74 | | | | 50 | |

Polyacetal = Copolymer of trioxane and 2.5% of butanediol formal, molecular weight 150,000
PBDF = Polybutanediol formal, molecular weight 50,000
PE = Polyethylene, molecular weight 150,000, d = 0.95 g/ml
PMMA = Polymethyl methacrylate, molecular weight 150,000, d = 1.17 g/ml, Lucryl G88 UV1 [BASF]
PS = Polystyrene, molecular weight 100,000, d = 1.04 g/ml, 168N [BASF]
PEG = Polyethylene glycol, molecular weight 800
PEO = Polyethylene oxide, molecular weight 400

TABLE II

| Example No. | Powder | Description | Mean Particle Size [μm] | Sintering Temperature [°C.] | Sintering Time [h] | Pore Size Distribution FIG. No. |
|---|---|---|---|---|---|---|
| 1a | $Al_2O_3$ | ALCOA CT3000SG | 0.7 | 600 | 2 | |
| 1b | $Al_2O_3$ | ALCOA CT3000SG | 0.7 | 800 | 2 | 1b |

TABLE II-continued

| Example No. | Powder | Description | Mean Particle Size [μm] | Sintering Temperature [°C.] | Sintering Time [h] | Pore Size Distribution FIG. No. |
|---|---|---|---|---|---|---|
| 1c | $Al_2O_3$ | ALCOA CT3000SG | 0.7 | 900 | 2 | |
| 1d | $Al_2O_3$ | ALCOA CT3000SG | 0.7 | 1100 | 2 | |
| 2 | $Al_2O_3$ | ALCOA CT3000SG | 0.7 | 800 | 2 | 2 |
| 3 | $Al^2O_3$ | ALCOA CT3000SG | 0.7 | 800 | 0.5 | 3 |
| 4 | 90% $Si_3N_4$ | HC STARCK, LC12 | 0.6 | 600 | 2 | 4 |
| | 5% $Y_2O_3$ | HC STARCK, grade fine | 0.5 | | | |
| | 5% $Al_2O_3$ | ALCOA CT3000SG | 0.7 | | | |
| 5 | $ZrO_2$ | TOSOH, TZ-3YS | 0.4 | 800 | 2 | 5 |
| 6 | $Al_2O_3$ | ALCOA CT3000SG | 0.7 | 1100 | 2 | 6 |
| 7 | $Al_2O_3$ | ALCOA, Tabular | 1–10 | 800 | 2 | 7 |
| 8 | SiC | NORTON, FCP13NCL | 0.8 | 1100 | 2 | 8 |
| B | $Al_2O_3$ | ALCOA, CT3000SG | 0.7 | 800 | 2 | 9 |
| | $Al_2O_3$ | RHONE POULENC, SPH512 | | | | |

TABLE IIIa

| Ex. No. | dm [nm] | dm/PS | d10 [nm] | d10/dm | d50 [nm] | d50/nm | d80 [nm] | d80/nm | d90 [nm] | d95 [nm] | d95/dm |
|---|---|---|---|---|---|---|---|---|---|---|---|
| 1a | 163 | 0.23 | 1824 | 11.3 | 170 | 1.0 | 127 | 0.8 | 76 | 35 | 0.2 |
| 1b | 169 | 0.24 | 3436 | 20.3 | 175 | 1.0 | 130 | 0.8 | 76 | 36 | 0.2 |
| 1c | 175 | 0.25 | 5305 | 30.3 | 178 | 1.0 | 140 | 0.8 | 99 | 65 | 0.4 |
| 1d | 173 | 0.25 | 7760 | 44.9 | 173 | 1.0 | 144 | 0.8 | 100 | 52 | 0.3 |
| 2 | 165 | 0.24 | 9000 | 54.5 | 170 | 1.0 | 136 | 0.8 | 111 | 75 | 0.5 |
| 3 | 160 | 0.23 | 1216 | 7.6 | 165 | 1.0 | 127 | 0.8 | 76 | 42 | 0.3 |
| 4 | 131 | 0.22 | 149 | 1.1 | 135 | 1.0 | 85 | 0.6 | 44 | 30 | 0.2 |
| 5 | 150 | 0.38 | 11360 | 75.7 | 155 | 1.0 | 126 | 0.8 | 87 | 29 | 0.2 |
| 6 | 172 | 0.25 | 1233 | 7.2 | 180 | 1.0 | 148 | 0.9 | 106 | 69 | 0.4 |
| 7 | bimodal pore diameter distribution, maxima at 150 μm/1 μm | | | | | | | | | | |
| | 1000 | | | | | | | | | | |
| | 150000 | | | | | | | | | | |
| 8 | 229 | 0.29 | 1390 | 6.1 | 235 | 1.0 | 188 | 0.8 | 130 | 87 | 0.4 |
| B | 169 | 0.24 | 3436 | 20.3 | 175 | 1.0 | 130 | 0.8 | 76 | 36 | 0.2 |
| | 224 | | 628 | 2.8 | 227 | 1.0 | 185 | 0.8 | 165 | 145 | 0.6 |

TABLE IIIb

| Ex. No. | WHH [nm] | WHH/dm | TPV [ml/g] | TPA [$m^2$/g] | CH [g] | Abrasion [%] | WA [ml/g] | BET [$m^2$/g] |
|---|---|---|---|---|---|---|---|---|
| 1a | 30 | 0.2 | 0.23 | 8.6 | | | | 6.4 |
| 1b | 30 | 0.2 | 0.23 | 8.7 | 4.9 | 3.7 | 0.2 | 5.6 |
| 1c | 30 | 0.2 | 0.23 | 6.3 | | | | 5.2 |
| 1d | 33 | 0.2 | 0.21 | 8.0 | | | | 4.3 |
| 2 | 30 | 0.2 | 0.22 | 6.9 | | | | |
| 3 | 33 | 0.2 | 0.23 | 8.9 | | | | |
| 4 | 29 | 0.2 | 0.31 | 17.7 | | | 0.38 | 23.1 |
| 5 | 26 | 0.2 | 0.12 | 5.5 | 2.4 | | 0.2 | 5.8 |
| 6 | 25 | 0.1 | 0.21 | 7.2 | 19.3 | 0.3 | 0.2 | 4.3 |
| 7 | 500 | 0.5 | 0.37 | 1.6 | | | | 2.2 |
| | 80000 | 0,5 | | | | | | |
| 8 | 60 | 0.3 | 0.22 | 6.2 | | | | 3.8 |

TABLE IIIb-continued

| Ex. No. | WHH [nm] | WHH/dm | TPV [ml/g] | TPA [$m^2/g$] | CH [g] | Abrasion [%] | WA [ml/g] | BET [$m^2/g$] |
|---|---|---|---|---|---|---|---|---|
| B | 25 | 0.1 | 0.23 | 8.7 | 4.9 | 3.7 | 0.2 | 5.6 |
| | 135 | 0.6 | 0.55 | 12 | | | | |

Mercury pressure porosimetry using Autopore II 9220 V3.03 in accordance with DIN 66133
PS: mean particle size
dm: mean pore diameter
TPV: total pore volume (300–0.005 μm)
TOA: total pore area (300–0.005 μm)
d10: pore diameter at 10% of total pore volume
d50: pore diameter at 50% of total pore volume
d80: pore diameter at 80% of total pore volume
d90: pore diameter at 90% of total pore volume
d95: pore diameter at 95% of total pore volume
WHH: width at half height of the pore size distribution
CH: cutting hardness
WA: water absorption
BET: specific surface area in accordance with DIN 66131
Abrasion: abrasion determination
WHH/dm: width at half height of the pore size distribution/mean pore diameter

Comparative Example A 586 g of $Si_3N_4$ (HC STARCK, LC12) were kneaded for 35 minutes with 32 g of $Y_2O_3$ (HC STARCK, grade fine), 32 g of $\alpha$-$Al_2O_3$ (ALCOA, CT3000SG), 150 g of $H_2O$ and 48 g of $HNO_3$ and extruded at from 45 to 150° C. to give 4 mm extrudates.

The extrudates were calcined in air for 2 hours at 600, 800 and 1100° C. During calcination, the extrudates disintegrated into powder (cutting hardness =0 kg).

Comparative Example B

Figure 9:
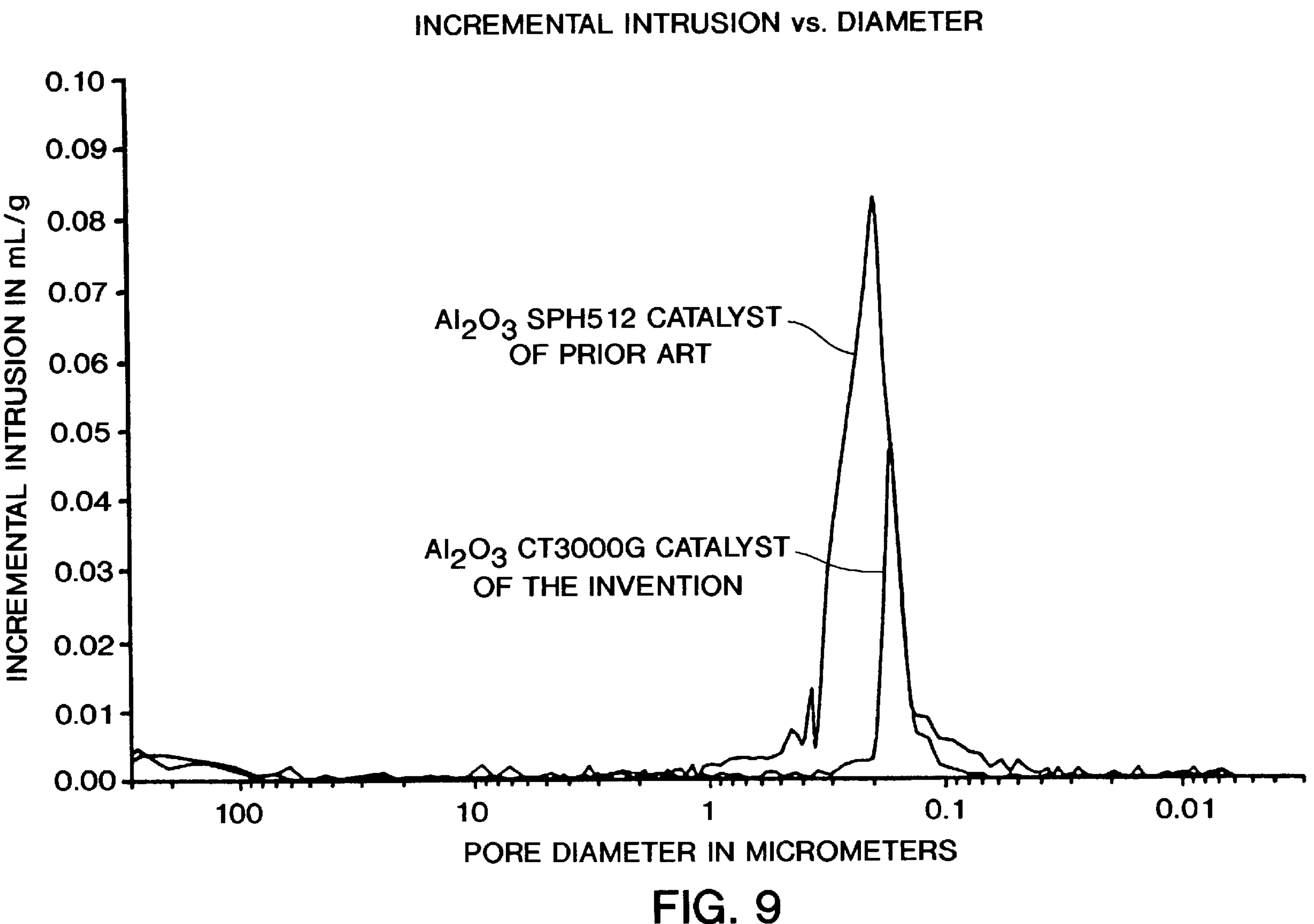

The commercial $\alpha$-$Al_2O_3$ catalyst support SPH512 from Rhone Poulenc has, at a comparative BET of 5.4 $m^2/g$ and a total pore volume (TPV) of 0.51 ml/g, a significantly broader pore distribution (see FIG. 9) than the $Al_2O_3$ catalyst support CT3000SG from ALCOA used according to the present invention and shown in Table IIIa and IIIb, Example No. 1b and FIG. 1*b*.

Comparative Example C

After conventional kneading and extruding, the $ZrO_2$ support has a lower hardness.

300 g of $ZrO_2$ powder (starting material from Example 5) from TOSOH, TZ-3YS, and 9 g of extrusion aid were admixed with 31 ml of water, densified in a kneader for 2.5 hours and subsequently shaped in an extruder to give 3 mm solid extrudates. The extrudates were dried for 2 hours at 120° C. and subsequently calcined in air for 2 hours at 800° C. (same calcination temperature as in Example 5).

The following properties were measured on the solid extrudates:

| Example | C | 5 |
|---|---|---|
| Cutting hardness [kg] | 0.6 | 2.4 |
| BET surface area [$m^2/g$] | 5.8 | 5.8 |
| Water absorption [ml/g] | 0.22 | 0.22 |
| Tamped density [g/ml] | 1.455 | 1.543 |

Comparative Example D

Lower hardness of a conventional $ZrO_2$ support even at high calcination temperatures.

100 g of high-surface-area $Zr(OH)_4$ (BET: 310 $m^2/g$) were admixed with 3 g of extrusion auxiliary and 45 ml of water and densified for 1.5 hours in a kneader. Attempts to shape this $ZrO_2$ support by extrusion were unsuccessful, since the extrudates disintegrated back into powder on drying (cutting hardness=0 kg). Therefore, the unextruded kneaded composition was calcined for 2 hours at 500° C. The BET surface area of the powder after calcination at 500° C. was 69.8 $m^2/g$. Calcination for 2 hours at 800° C. gave a BET surface of 11.2 $m^2/g$.

Example No. 9 (non-steady-state Deacon process)
Catalyst 1
Cu-K-Fe-Na on $Si_3N_4$ support
Production of $Si_3N_4$ support 900 g of $Si_3N_4$ (HC STARCK; LC12) were kneaded at 180° C. with 50 g of $Y_2O_3$ (HC STARCK; grade fine) and 50 g of $Al_2O_3$ (ALCOA; CT3000SG) together with a binder based on polyacetal, comprising 276 g of polyoxymethylene copolymer (POM/PBDF) of trioxane and 2.5% by weight of butanediol formal having an average molecular weight of 150,000, and with 69 g of polybutanediol formal having a molecular weight of 50,000 and 50 g of polyethylene glycol having a molecular weight of 800 as auxiliary, granulated and pyrolyzed at 600° C. for 2 hours under $N_2$ in a muffle furnace and pre-sintered at 1000° C. for 2 hours. This gave an $Si_3N_4$ support having a BET surface area of 22.3 $m^2/g$ and a water absorption of 0.608 ml/g.

Impregnation of $Si_3N_4$ support 111.5 g of $Si_3N_4$ granules were impregnated twice with 67.8 ml each time of a solution of 7.06 g of $CuCl_2.2H_2O$, 5.58 g of KCl, 5.58 g of NaCl and 9.29 g of $FeCl_3.6H_2O$ dissolved in distilled water (total solution 135.6 ml), dried for 16 hours at 120° C. (after each impregnation step) and calcined for 3 hours at 450° C. This gave brown granules having a BET surface area of 9.93 $m^2$/g. The tamped density was 0.978 g/ml (0.5 to 1 mm grain size).

Further impregnation with an $FeCl_3$-NaCl solution 25 g of the previously impregnated $Si_3N_4$ support were impregnated once with a solution of 1.39 g of NaCl and 2.21 g of $FeCl_3.6H_2O$ in 15.9 ml of water, dried for 16 hours at 120° C. and calcined for 3 hours at 450° C. The tamped density of the catalyst was 0.995 g/ml (0.5 to 1 mm grain size). The catalyst contained 1.8% by weight of copper and 3% by weight of iron.

Catalyst 2

Cu-K-Fe-Na on $Si_3N_4$ support

Production of the $Si_3N_4$ support 1000 g of SiC (H. C. STARCK; UF15) were kneaded at 180° C. with a binder based on polyacetal, comprising 281 g of polyoxymethylene copolymer (POM/PBDF) of trioxane and 2.5% by weight of butanediol formal having an average molecular weight of 150,000, and with 70 g of polybutanediol formal having a molecular weight of 50,000 and 50 g of polyethylene glycol having a molecular weight of 800 as auxiliary, melted on a roll mill to a 0.5 mm thick sheet, broken up into platelets and these were pyrolyzed and presintered at 600° C. for 2 hours under $N_2$ in a rotary tube furnace. This gave an SiC support having a BET surface area of 22.3 $m^2$/g and a water absorption of 0.35 ml/g.

Impregnation of the SiC support 150 g of SiC platelets were impregnated twice with 53 ml each time of a solution of 23.7 g of $CuCl_2.2H_2O$, 10.38 g of KCl, 42.78 g of $FeCl_3.6H_2O$ and 9.26 g of NaCl dissolved in distilled water (total solution 106 ml), dried for 16 hours at 120° C. (after each impregnation step) and calcined for 3 hours at 450° C.

Further impregnation with an $FeCl_3$-NaCl solution 70 g of the previously impregnated SiC platelets were impregnated once with 22 ml of a solution of 3.92 g of NaCl and 18.22 g of $FeCl_3.6H_2O$ dissolved in distilled water (total solution 25 ml), dried for 16 hours at 120° C. and calcined for 3 hours at 450° C. This gave reddish brown platelets containing 3.3% by weight of copper and 7.8% by weight of iron.

General procedure for the non-steady-state preparation of chlorine

A heated tube reactor having a 20 ml fixed bed of catalyst was charged with a size fraction of 0.5–1 mm. After the loading phase using a dry HCl stream and a subsequent flushing phase using inert gas ($N_2$ or $CO_2$), regeneration (dechlorination) was carried out using air or pure oxygen. This cycle was repeated.

The HCl concentration and the chlorine concentration were measured continuously at high time resolution using on-line IR analysis and on-line UV analysis respectively. The integrated amount of chlorine liberated during dechlorination could, for checking purposes, be additionally determined by wet chemical methods (iodometrically).

The results are summarized in Tables 1 and 2.

TABLE 1

Catalyst 1

HCl loading: 250 ml HCl/h/ml catalyst 1; 5 minutes' countercurrent flushing with 60 standard 1/h of $CO_2$; regeneration with 5 standard 1/h of pure $O_2$ at 250 ml $O_2$/h/ml catalyst; 23 cycles

| Reactor | Loading | | | Dechlorination | | | | | |
|---|---|---|---|---|---|---|---|---|---|
| temperature [° C.] | HCl concentration [vol. %] | Loading time [min] | Loading time [min] | Maximum chlorine concentration [vol. %] | Mean chlorine concentration [vol. %] | Maximum residual HCl concentration [vol. %] | Mean residual HCl concentration [vol. %] | Dechlorination time (to < 10 vol. % $Cl_2$) [min] | Total space-time yield [kg $Cl_2$/t cat.h] |
| 425 | 50 | 6 | 39.5 | 50 | 32.9 | 1.2 | 0.65 | 7.8 | 44.3 |
| 425 | 65 | 8 | 49.5 | 62 | 35.5 | 2 | 1.1 | 10 | 51.1 |
| 425 | 73 | 9.7 | 47.3 | 64 | 36.4 | 1.6 | 0.8 | 10 | 54.4 |
| 440 | 73 | 10 | 45 | 61 | 35.8 | 2.8 | 1.5 | 9.3 | 52 |
| 450 | 73 | 11 | 44.6 | 65 | 37.4 | 2.5 | 1.2 | 9 | 53.7 |
| 460 | 73 | 11.5 | 44.4 | 64 | 38.6 | 2.5 | 1.3 | 9 | 56 |
| 460 | 100 | 15 | 25 | 58 | 35.3 | 2.5 | 1.2 | 9 | 73.3 |

TABLE 2

Catalyst 2
HCl loading: 250 ml HCl/h/ml catalyst 2; 5 minutes' countercurrent flushing with 60 standard 1/h of $N_2$; regeneration using 5 standard 1/h of pure $O_2$

| | Loading | | | | Declorination | | | | Dechlorination | |
|---|---|---|---|---|---|---|---|---|---|---|
| Reactor temperature | HCl concentration | Loading time | Loading time | Reactor temperature | Chlorine concentration [vol. %] | | Residual HCl concentration [vol. %] | | time (to < 10 vol. % $Cl_2$) | Total space-time yield |
| [° C.] | [vol. %] | [min] | [min] | [° C.] | maximum | mean | maximum | mean | [min] | [kg $Cl_2$/t cat.h] |
| 380 | 100 | 15 | 15 | 400 | 26.9 | 21.9 | 1.4 | 1.2 | 10 | 47.2 |
| 360 | 100 | 16 | 17 | 380 | 19.8 | 17.2 | 1.2 | 0.95 | 12 | 38.7 |
| 390 | 100 | 16 | 17 | 410 | 30.7 | 24.5 | 1.3 | 1.15 | 8 | 43 |
| 390 | 100 | 16 | 13 | 410 | 32.8 | 24.5 | | | 8 | 36.3 |
| | | | | | + 10 left standing under HCl with closed reactor outlet | | | | | |
| 400 | 100 | >10 | 10 | 400 | 24.1 | 19.4 | | | 6.5 | 28 |
| | | | | | + 6 left standing under HCl with closed reactor outlet | | | | | |
| 380 | 100 | 10.5 | 10 | 400 | 28.6 | 23.5 | 1.7 | 1.6 | 8.5 | 44.2 |
| | | | | | + 6 left standing under HCl with closed reactor outlet | | | | | |

Comparative Example E [non-steady-state Deacon process]

Comparative catalyst
(Cu-Fe-K on $Al_2O_3$ support)

200 g of $Al_2O_3$ (Pural SCF rings) were impregnated with 92 ml of a solution of 32.16 g of $CuCl_2.2H_2O$ 58 g of $FeCl_3.6H_2O$ 30g of KCl and 114 ml of water (water absorption=0.46 ml/g), dried for 16 hours at 120° C., calcined for 3 hours at 450° C. and subsequently impregnated with the remaining 85 ml of solution, dried for 16 hours at 120° C. and calcined for 3 hours at 450° C. The comparative catalyst C contained 3.8% by weight of Cu and 4.5% by weight of Fe; tamped density: 0.974 g/ml (0.5–1 mm grain size); BET surface area: 68.6 $m^2$/g.

An attempt to impregnate the catalyst for a third time resulted in it disintegrating.

Cu-Fe-K on $Al_2O_3$ support

Using a method similar to the general procedure for the non-steady-state preparation of chlorine of Examples 1 to 3, the comparative catalyst Cu-Fe-K on $Al_2O_3$ was loaded at 365° C. and HCl gas flows from 4 to 5 standard l/h containing 25% of HCl (the support did not withstand higher HCl concentrations) at an HCl breakthrough time of from 10 to 14 minutes. The dechlorination was carried out using 20 standard l/h of air at a regeneration temperature of 365° C. at dechlorination times of 60 minutes and an integrated amount of chlorine of 0.9 g, which corresponded to a space-time yield of 34 kg chlorine/t cat.h.

If the dechlorination was carried out using 20 standard l/h of air at a regeneration temperature of 380° C., dechlorination times of 35 minutes and an integrated amount of chlorine of 0.7 g were found, corresponding to a space-time yield of 38 kg chlorine/t cat.h.

At a reactor temperature of 400° C. during loading and dechlorination, a maximum chlorine concentration of 8% by volume of $Cl_2$ and a mean chlorine concentration of 4% by volume of $Cl_2$ at dechlorination times (to <2% by volume of chlorine) of 25 minutes were obtained. The integrated amount of chlorine liberated was 1 g. The maximum measured space-time yield was 40 kg chlorine/t cat.h.

We claim:

1. A monomodal or polymodal catalyst support or catalyst having a BET specific surface area of from 0.01 to 250 $m^2$/g and a monomodal or polymodal pore size distribution having a mean pore diameter of from 50 to 300,000 nm measured by the mercury pressure porosimetry method, wherein the pore size distribution fulfills at least one of the following conditions a) to d)

a) from 10 to 95% of the pore volume is from about 0.2 to 100 times the mean pore diameter, b) from 10 to 80% of the pore volume is from about 0.8 to 100 times the mean pore diameter, c) from 50 to 95% of the pore volume is from about 0.2 to 1 times the mean pore diameter, d) from 50 to 80% of the pore volume is from about 0.8 to 1 times the mean pore diameter, and the condition e) the width at half height of the pore size distribution is less than 0.6 times the mean pore diameter.

2. A process for producing a monomodal or polymodal catalyst support or catalyst as defined in claim 1, comprising the steps of shaping a mixture of A) from 15 to 70% by volume of at least one of I) an inorganic powder selected from the group of oxides, nitrides, carbides, silicates, aluminosilicates of the elements beryllium, magnesium, calcium, strontium, barium, boron, aluminum, gallium, indium, thallium, silicon, germanium, tin, lead, antimony, selenium, tellurium, polonium, astatine, iron, cobalt, nickel, ruthenium, rhodium, palladium, osmium, iridium, platinum, copper, silver, gold, zinc, cadmium, mercury, scandium, yttrium, lanthanum, actinium, titanium, zirconium, hafnium, vanadinium, niobium, tantalum, chromium, molybdenum, tungsten, manganese, technetium, rhenium, cerium, praseodymium and mixtures thereof, II) a metallic powder selected from compounds metals and alloys of the elements boron, aluminum, gallium, indium, thallium, silicon, germanium, tin, lead, antimony, selenium, tellurium, polonium, neodymium, samarium, dysprosium, astatine, iron, cobalt, Raney cobalt, nickel, Raney nickel, ruthenium, rhodium, palladium, osmium, iridium, platinum, copper, silver, gold, zinc, cadmium, mercury, scandium, yttrium, lanthanum, actinium, titanium, zirconium, hafnium, vanadinium, niobium, tantalum, chromium, molybdenum, tungsten, manganese, technetium, rhenium, cerium, praseodymium, WC, TiC, TaC, VC and mixtures thereof, WC-cobalt, TiC-cobalt, TaC-cobalt, VC-cobalt and mixtures thereof and also carbon, III) an active component selected from the group of the inorganic acids, the metals lithium, sodium, potassium, rubidium, cesium, francium, beryllium, magnesium, calcium, strontium, barium, boron, aluminum, gallium, indium, thallium, silicon, germanium, tin, lead, arsenic, antimony, bismuth, selenium, tellurium, polonium, astatine, iron, cobalt, Raney cobalt, nickel, Raney nickel, ruthenium, rhodium, palladium, osmium, iridium, platinum, copper, silver, gold, zinc, cadmium, mercury, scandium, yttrium, lanthanum, actinium, titanium, zirconium, hafnium, vanadinium, niobium, tantalum, chromium, molybdenum, tungsten, manganese, technetium, rhenium, cerium, praseodymium, mixtures thereof, and their borates, carbonates, silicates, nitrates, phosphates, arsenates, antimonates, bismuthates, sulfates, selenates, tellurates, vanadates, molybdates, niobates, chromates, oxides, hydroxides, halides, sulfides, selenides, tellurides, nitrides, phosphides, arsenides, acetates, acetylacetonates, palladates, platinates, cyanides, thiocyanates, manganates, rhenates, osmates, carbides, suicides, borides, and ammonium compounds and all component mixtures thereof and IV) an organic powder selected from the group of Teflon and polyimide B) from 30 to 85% by volume of a binder selected from the group of a polyethylene polymer, a polypropylene polymer, a copolymer of one selected from ethylene, propylene, 1-butene and isobutene, a polystyrene copolymer, a polymethyl methacrylate copolymer, a polyethylene oxide copolymer, an ethylene-vinyl acetate copolymer, and a mixture of $B_1$) from 50 to 100% by weight of a polyoxymethylene homopolymer or copolymer and $B_2$) from 0 to 50% by weight of a polymer homogeneously dissolved in $B_1$) or dispersed in $B_1$) at a mean particle size of less than 1 $\mu$m and C) from 0 to 15% by volume of a dispersant, removing the binder by pyrolysis at from 300 to 600° C. and subsequent presintering at from 600 to 1400° C. and, optionally, applying active components III to the component A) or to the presintered composition by single or multiple steeping, impregnating, spray impregnating, precipitating on, hicoating, washcoating or spray drying, wherein the catalyst support or catalyst after the pyrolytic removal of the binder has a BET specific surface area of from 0.01 to 250 $m^2/g$ and a pore size distribution of from 50 to 300,000 nm measured by the mercury pressure porosimetry method.

3. A process for producing a polymodal catalyst support or catalyst as claimed in claim 2, wherein said organic powder has a polymodal particle size distribution or internal porosity.

4. A process for producing a monomodal or polymodal catalyst support or catalyst as claimed in claim 2, containing at least one or more members selected from the group of aluminum, iron, cobalt, nickel, palladium, platinum, copper, silver, molybdenum, zinc, titanium, zirconium, tungsten, niobium, chromium, carbon, an inorganic powder selected from the group of $Al_2O_3$, MgO, $SiO_2$, $TiO_2$, $Y_2O_3$, $ZrO_2$, ZnO, $Fe_3O_4$, $Fe_2O_3$, CoO, $Co_2O_3$, $Cr_2O_3$, NiO, $B_2O_3$, $Ce_2O_3$, $CeO_2$, $Pr_2O_3$, $B_4C$, SiC, WC, TiC, TaC, $Si_3N_4$, AlN, BN, TiN, and ZrN, and a mixture of two or more thereof.

5. A process for producing a monomodal or polymodal catalyst support or catalyst as claimed in claim 2, containing at least one or more members selected from the group of iron, cobalt, nickel, chromium, molybdenum, and titanium, an inorganic powder selected from the group of SiC, $Si_3N_4$, BN, $B_4C$, WC, TiC, TiN, ZrN, and AlN, and a mixture of two or more thereof.

6. A process for producing a monomodal or polymodal catalyst support or catalyst as claimed in claim 2, containing an inorganic powder selected from the group consisting of SiC, $Si_3N_4$ and a mixture thereof.

7. A process for producing a monomodal or polymodal catalyst support or catalyst as claimed in claim 2, comprising the step of shaping the mixture of A), B) and C) by a method selected from the group of granulation, pressing, rolling, extrusion, injection molding and continuous casting at from 80 to 250° C.

8. A monomodal or polymodal catalyst support or catalyst obtained by the process according to claim 2.

9. A process for producing a monomodal or polymodal catalyst support or catalyst as claimed in claim 2, wherein said catalyst or catalyst support is a monolith or a bed of individual parts with a shape comprising Raschig rings, saddles, star rings, perforated and ribbed geometric bodies, wherein the said ribbed geometric bodies are rings, spheres, cuboids, cubes, cones, pyramids, prisms, octahedra, cylinders, truncated pyramids, truncated cones, wagon wheel profiles, window frame profiles and mixtures thereof.

* * * * *